United States Patent [19]

Mistui et al.

[11] 4,262,013

[45] Apr. 14, 1981

[54] MEVALONOLACTONE DERIVATIVES AND PROCESS FOR THE PREPARATION THEREOF

[75] Inventors: Seiji Mistui; Akira Ogiso; Akira Indo, all of Hiromachi, Japan

[73] Assignee: Sankyo Company Limited, Tokyo, Japan

[21] Appl. No.: 63,549

[22] Filed: Aug. 3, 1979

Related U.S. Application Data

[62] Division of Ser. No. 903,575, May 8, 1978, Pat. No. 4,198,425.

[30] Foreign Application Priority Data

May 24, 1977 [JP] Japan .................................. 52-60110

[51] Int. Cl.$^3$ ............................................. C07D 309/30
[52] U.S. Cl. ................................ 424/279; 260/343.5; 542/413; 542/441
[58] Field of Search ................ 424/279; 542/441, 413; 260/343.5

[56] References Cited

U.S. PATENT DOCUMENTS

| | | | |
|---|---|---|---|
| 3,346,594 | 10/1967 | Merijan et al. | 424/279 |
| 3,522,245 | 7/1970 | Brinkhoff | 424/279 |
| 4,004,022 | 1/1977 | Kumita et al. | 424/279 |

FOREIGN PATENT DOCUMENTS 1214936 12/1970 United Kingdom .

OTHER PUBLICATIONS

Reffstrup et al., Acta Chemica Scand. B., 30, (1976), pp. 613–618.
Cognacq, Chem. Abst., 76, (1972), #113068.

*Primary Examiner*—Arthur P. Demers
*Attorney, Agent, or Firm*—Frishauf, Holtz, Goodman & Woodward

[57] ABSTRACT

This invention concerns novel mevalonolactone derivatives having the formula

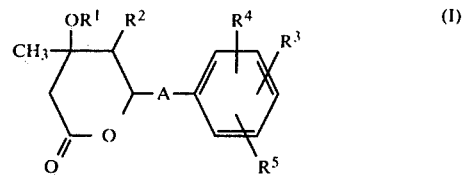

wherein A represents a direct linkage, methylene, ethylene, trimethylene or vinylene group; $R^1$ represents hydrogen atom, an aliphatic acyl group, benzoyl group, or a benzoyl group substituted with hydroxy, lower alkoxy, aliphatic acyloxy or halogen; $R^2$ represents hydrogen atom, a halogen atom or methyl group; and $R^3$, $R^4$ and $R^5$ are same or different and each represents hydrogen atom, a halogen atom, a lower alkyl group with or without halogen as the substituent, phenyl group, or a phenyl group substituted with halogen, lower alkoxy, aliphatic acyloxy or lower alkyl with or without halogen, or a group represented by the formula $R^6O$— (in the formula, $R^6$ means hydrogen atom, an aliphatic acyl group, benzoyl group, phenyl group, a phenylalkyl group, cinnamyl group, or a group of benzoyl, phenyl, phenylalkyl or cinnamyl in all of which the aromatic ring is substituted with hydroxy, halogen, lower alkoxy, aliphatic acyloxy or lower alkyl with or without halogen as the substituent, or a lower alkyl group with or without halogen as the substituent).

The compounds are useful for the treatment of hyperlipidemia.

They may be prepared by halo-lactonizing the corresponding γ,δ-unsaturated carboxylic acid derivatives and optionally dehalogenating the resulting product, or lactonizing the corresponding δ-hydroxy-carboxylic acid derivatives.

11 Claims, No Drawings

MEVALONOLACTONE DERIVATIVES AND PROCESS FOR THE PREPARATION THEREOF

This is a division of application Ser. No. 903,575, filed May 8, 1978 issued as U.S. Pat. No. 4,198,425 on Apr. 15, 1980.

The present invention relates to novel mevalonolactone derivatives that are useful for the treatment of hyperlipidemia and to processes for their preparation.

More particularly, this invention relates to mevalonolactone derivatives having the general formula

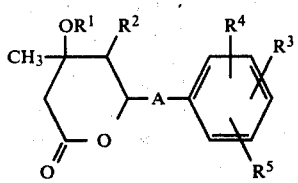

(wherein A represents a direct linkage, methylene, ethylene, trimethylene or vinylene group; $R^1$ represents hydrogen atom, an aliphatic acyl group containing from 2 to 8 carbon atoms, benzoyl group, or a benzoyl group substituted with hydroxy, alkoxy containing from 1 to 4 carbon atoms, aliphatic acyloxy containing from 2 to 8 carbon atoms or halogen; $R^2$ represents hydrogen atom, a halogen atom or methyl group; and $R^3$, $R^4$ and $R^5$ are same or different and each represents hydrogen atom, a halogen atom, an alkyl group containing from 1 to 4 carbon atoms with or without halogen as the substituent, phenyl group, or a phenyl group substituted with halogen, alkoxy containing from 1 to 4 carbon atoms, aliphatic acyloxy containing from 2 to 8 carbon atoms or alkyl containing from 1 to 4 carbon atoms with or without halogen, or a group represented by the formula $R^6O-$ (in the formula, $R^6$ means hydrogen atom, an aliphatic acyl group containing from 2 to 8 carbon atoms, benzoyl group, phenyl group, a phenylalkyl group comprising an alkylene chain having from 1 to 3 carbon atoms, cinnamyl group, or a group of benzoyl, phenyl, phenylalkyl comprising an alkylene chain having from 1 to 3 carbon atoms or cinnamyl in all of which the aromatic ring is substituted with hydroxy, halogen, alkoxy containing from 1 to 4 carbon atoms, aliphatic acyloxy containing from 2 to 8 carbon atoms or alkyl containing from 1 to 4 carbon atoms with or without halogen as the substituent, or an alkyl group containing from 1 to 4 carbon atoms with or without halogen as the substituent)).

Preferable examples of $R^1$ in the above general formula (I) are hydrogen atom; an aliphatic acyl group containing from 2 to 8 carbon atoms such as acetyl, propionyl, n-butylryl, isobutyryl, α-methylbutyryl, caproyl or octanoyl group; benzoyl group; (o-, m-, p-)hydroxybenzoyl group; a benzoyl group substituted with alkoxy radical containing from 1 to 4 carbon atoms such as (o-, m-, p-)methoxybenzoyl, (o-, m-, p-)ethoxybenzoyl, (o-, m-, p-)isopropoxybenzoyl or (o-, m-, p-)tert-butoxybenzoyl group; a benzoyl group substituted with aliphatic acyloxy radical containing from 2 to 8 carbon atoms such as (o-, m-, p-)acetoxybenzoyl, (o-, m-, p-)propionyloxybenzoyl, (o-, m-, p-)isobutyryloxybenzoyl, (o-, m-, p-)α-methylbutyryloxybenzoyl, (o-, m-, p-)caproyloxybenzoyl or (o-, m-, p-)octanoyloxybenzoyl group; or a benzoyl group substituted with halogen atom such as (o-, m-, p-)chlorobenzoyl or (o-, m- p-)bromobenzoyl group. Preferable examples of $R^2$ are hydrogen atom; a halogen atom such as chlorine or bromine; or methyl group. As preferable examples of $R^3$ are mentioned hydrogen atom; a halogen atom such as fluorine, chlorine or bromine atom; an alkyl group containing from 1 to 4 carbon atoms such as methyl, ethyl, n-propyl, isopropyl or tert-butyl group; an alkyl group containing from 1 to 4 carbon atoms substituted with halogen atom such as trifluoromethyl or 2,2,2-trifluoroethyl group; phenyl group; a phenyl group substituted with halogen atom such as (o-, m-, p-)chlorophenyl or (o-, m-, p-)bromophenyl group; a phenyl group substituted with alkoxy radical containing from 1 to 4 carbon atoms such as (o-, m-, p-)methoxyphenyl, (o-, m-, p-)ethoxyphenyl, (o-, m-, p-)isopropoxyphenyl or (o-, m-, p-)tert-butoxyphenyl group; a phenyl group substituted with aliphatic acyloxy radical containing from 2 to 8 carbon atoms such as (o-, m-, p-)acetoxyphenyl, (o-, m-, p-)propionyloxyphenyl, (o-, m-, p-)isobutyryloxyphenyl, (o-, m-, p-)α-methylbutyryloxyphenyl, (o-, m-, p-)caproyloxyphenyl or (o-, m-, p-)octanoyloxyphenyl group; a phenyl group substituted with alkyl radical containing from 1 to 4 carbon atoms such as (o-, m-, p-)methylphenyl, (o-, m-, p-)ethylphenyl, (o-, m-, p-)isopropylphenyl or (o-, m-, p-)tert-butylphenyl group; a phenyl group substituted with halogen-containing alkyl radical having from 1 to 4 carbon atoms such as (o-, m-, p-)trifluoromethylphenyl, (o-, m-, p-)trichloromethylphenyl or (o-, m-, p-)2,2,2-trifluoroethylphenyl group; hydroxy group; an aliphatic acyloxy group containing from 2 to 8 carbon atoms such as acetoxy, propionyloxy, isobutyryloxy, α-methylbutyryloxy, caproyloxy or octanoyloxy; benzoyloxy group; (o-, m-, p-)hydroxybenzoyloxy group; a benzoyloxy group substituted with halogen atom such as (o-, m-, p-)fluorobenzoyloxy, (o-, m-, p-)chlorobenzoyloxy; a benzoyloxy group substituted with alkoxy radical containing from 1 to 4 carbon atoms such as (o-, m-, p-)methoxybenzoyloxy, (o-, m-, p-)ethoxybenzoyloxy, (o-, m-, p-)isopropoxybenzoyloxy or (o-, m-, p-)tert-butoxybenzoyloxy group; a benzoyloxy group substituted with aliphatic acyloxy radical containing from 2 to 8 carbon atoms such as (o-, m-, p-)acetoxybenzoyloxy, (o-, m-, p-)propionyloxybenzoyloxy, (o-, m-, p-)isobutyryloxybenzoyloxy, (o-, m-, p-)α-methylbutyryloxybenzoyloxy, (o-, m-, p-)caproyloxybenzoyloxy or (o-, m-, p-)octanoyloxybenzoyloxy group; a benzoyloxy group substituted will alkyl radical containing from 1 to 4 carbon atoms such as (o-, m-, p-)methylbenzoyloxy, (o-, m-, p-)ethylbenzoyloxy, (o-, m-, p-)isopropylbenzoyloxy or (o-, m-, p-)tert-butylbenzoyloxy group; a benzoyloxy group substituted with halogen-containing alkyl radical having from 1 to 4 carbon atoms such as (o-, m-, p-)trifluoromethylbenzoyloxy, (o-, m-, p-)trichloromethylbenzoyloxy or (o-, m-, p-)2,2,2-trifluoroethylbenzoyloxy group; phenoxy group; (o-, m-, p-)hydroxyphenoxy group; a phenoxy group substituted with halogen atom such as (o-, m-, p-)fluorophenoxy or (o-, m-, p-)chlorophenoxy group; a phenoxy group substituted with alkoxy radical containing from 1 to 4 carbon atoms such as (o-, m-, p-)methoxyphenoxy, (o-, m-, p-)ethoxyphenoxy, (o-, m-, p-)isopropoxyphenoxy or (o-, m-, p-)tertbutoxyphenoxy group; a phenoxy group substituted with aliphatic acyloxy radical containing from 2 to 8 carbon atoms such as (o-, m-, p-)acetoxyphenoxy, (o-, m-, p-)propionyloxyphenoxy, (o-, m-, p-)isobutyryloxyphenoxy, (o-, m-, p-)α-methylbutyryloxyphenoxy, (o-, m-, p-)caproyloxyphenoxy or (o-, m-, p-)octanoyloxyphenoxy group; a phenoxy group substituted with alkyl radical containing from 1 to 4 carbon atoms such as (o-, m-, p-)methylphenoxy, (o-, m-, p-)ethylphenoxy, (o-, m-, p-)isopropylphenoxy or (o-, m-, p-)tert-butylphenoxy group; a phenoxy group substituted with halogen-containing alkyl group having from 1 to 4 carbon atoms such as (o-, m-, p-)trifluoromethylphenoxy, (o-, m-, p-)trichloromethylphenoxy or (o-, m-, p-)2,2,2-trifluoroethylphenoxy group; a phenylalkoxy group comprising an alkylene chain containing from 1 to 3 carbon atoms such as benzyloxy, phenethyloxy or phenylpropyloxy group; a phenylalkoxy group comprising an alkylene chain containing from 1 to 3 carbon atoms in which the aromatic ring is substituted with hydroxy radical, such as (o-, m-, p-)hydroxybenzyloxy, (o-, m-, p-)hydroxyphenethyloxy or (o-, m-, p-)hydroxyphenylpropyloxy group; a phenylalkoxy group comprising an alkylene chain containing from 1 to 3 carbon atoms in which the aromatic ring is substituted with halogen atom, such as (o-, m-, p-)fluorobenzyloxy, (o-, m-, p-)chlorobenzyloxy, (o-, m-, p-)chlorophenethyloxy, (o-, m-, p-)fluorophenylpropyloxy group; a phenylalkoxy group comprising an alkylene chain containing from 1 to 3 carbon atoms in which the aromatic ring is substituted with alkoxy radical containing from 1 to 4 carbon atoms, such as (o-, m-, p-)methoxybenzyloxy, (o-, m-, p-)methoxyphenethyloxy, (o-, m-, p-)methoxyphenylpropyloxy, (o-, m-, p-)ethoxybenzoyloxy, (o-, m-, p-)ethoxyphenethyloxy), (o-, m-, p-)isopropoxybenzyloxy, (o-, m-, p-)isopropoxyphenethyloxy or (o-, m-, p-)tert-butoxybenzyloxy group; a phenylalkoxy group comprising an alkylene chain containing from 1 to 3 carbon atoms in which the aromatic ring is substituted with aliphatic acyloxy radical containing from 2 to 8 carbon atoms, such as (o-, m-, p-)acetoxybenzyloxy, (o-, m-, p-)acetoxyphenethyloxy, (o-, m-, p-)acetoxyphenylpropyloxy, (o-, m-, p-)propionyloxybenzyloxy, (o-, m-, p-)isobutyryloxybenzyloxy, (o-, m-, p-)isobutyryloxyphenethyloxy, (o-, m-, p-)α-methylbutyryloxybenzyloxy, (o-, m-, p-)caproyloxybenzyloxy or (o-, m-, p-)octanoyloxybenzyloxy group; a phenylalkoxy group comprising an alkylene chain containing from 1 to 3 carbon atoms in which the aromatic ring is substituted with alkyl radical containing from 1 to 4 carbon atoms, such as (o-, m-, p-)methylbenzyloxy, (o-, m-, p-)methylphenethyloxy, (o-, m-, p-)methylphenylpropyloxy, (o-, m-, p-)ethylbenzyloxy, (o-, m-, p-)ethylphenethyloxy, (o-, m-, p-)isopropylbenzyloxy, (o-, m-, p-)isopropylphenethyloxy or (o-, m-, p-)tert-butylbenzyloxy group; a phenylalkoxy group comprising an alkylene chain containing from 1 to 3 carbon atoms in which the aromatic ring is substituted with halogen-containing alkyl radical having from 1 to 4 carbon atoms, such as (o-, m-, p-)trifluoromethylbenzyloxy, (o-, m-, p-)trifluoromethylphenethyloxy, (o-, m-, p-)trifluoromethylphenylpropyloxy, (o-, m-, p-)trichloromethylbenzyloxy or (o-, m-, p-)2,2,2-trifluoroethylbenzyloxy group; cinnamyloxy group; (o-, m-, p-)hydroxycinnamyloxy group; a cinnamyloxy group in which the aromatic ring is substituted with halogen atom, such as (o-, m-, p-)fluorocinnamyloxy or (o-, m-, p-)chlorocinnamyloxy group; a cinnamyloxy group in which the aromatic ring is substituted with alkoxy radical containing from 1 to 4 carbon atoms, such as (o-, m-, p-)methoxycinnamyloxy, (o-, m-, p-)ethoxycinnamyloxy, (o-, m-, p-)isopropoxycinnamyloxy or (o-, m-, p-)tert-butyoxycinnamyloxy group; a cinnamyloxy group in which the aromatic ring is substituted with aliphatic acyloxy radical containing from 2 to 8 carbon atoms, such as (o-, m-, p-)acetoxycinnamyloxy, (o-, m-, p-)propionyloxycinnamyloxy, (o-, m-, p-)isobutyryloxycinnamyloxy, (o-, m-, p-)α-methylbutyryloxycinnamyloxy, (o-, m-, p-)caproyloxycinnamyloxy or (o-, m-, p-)octanoyloxycinnamyloxy group; a cinammyloxy group in which the aromatic ring is substituted with alkyl radical containing from 1 to 4 carbon atoms, such as (o-, m-, p-)methylcinnamyloxy, (o-, m-, p-)ethylcinnamyloxy, (o-, m-, p-)isopropylcinnamyloxy or (o-, m-, p-)tert-butylcinnamyloxy group; a cinnamyloxy group in which the aromatic ring is substituted with halogen-containing alkyl radical having from 1 to 4 carbon atoms, such as (o-, m-, p-)trifluoromethylcinnamyloxy, (o-, m-, p-)trichloromethylcinnamyloxy or (o-, m-, p-)2,2,2-trifluoroethylcinnamyloxy group; an alkoxy group containing from 1 to 4 carbon atoms such as methoxy, ethoxy, n-propoxy, isopropoxy or tert-butoxy group; a halogen-containing alkoxy group having from 1 to 4 carbon atoms such as trifluoromethoxy, trichloromethoxy or 2,2,2-trifluoroethoxy group.

More preferred compounds of the above general formula (I) are those in which A represents a direct linkage, ethylene, trimethylene or vinylene group; $R^1$ is hydrogen atom, an aliphatic acyl group containing from 2 to 4 carbon atoms, benzoyl group, or a benzoyl group substituted with fluorine, chlorine or bromine; $R^2$ represents hydrogen atom, bromine atom or methyl group; $R^3$ is hydrogen atom, fluorine atom, chlorine atom, bromine atom, trifluoromethyl group, 2,2,2-trifluoroethyl group, an alkyl group containing from 1 to 4 carbon atoms, hydroxy group, an aliphatic acyloxy group containing from 2 to 4 carbon atoms, phenyl group, benzoyloxy group, phenoxy group, benzyloxy group, phenethyloxy group, cinnamyloxy group, or a group of phenyl, benzoyloxy, phenoxy, benzyloxy, phenethyloxy or cinnamyloxy in all of which the atomatic ring is substituted with fluorine, chlorine, bromine, trifluoromethyl or 2,2,2-trifluoroethyl, or an alkoxy group containing from 1 to 4 carbon atoms; and $R^4$ and $R^5$ are same or different and each represents hydrogen atom, an alkyl group containing from 1 to 4 carbon atoms, hydroxy group, an aliphatic acyloxy group containing from 2 to 4 carbon atoms, benzoyloxy group, phenoxy group, benzyloxy group, phenethyloxy group, cinnamyloxy group, or a group of benzoyloxy, phenoxy, benzyloxy, phenethyloxy or cinnamyloxy in all of which the aromatic ring is substituted with fluorine, chlorine, bromine, trifluoromethyl or 2,2,2-trifluoroethyl, or an alkoxy group containing from 1 to 4 carbon atoms.

The most preferred compounds are those in which A represents ethylene, trimethylene or vinylene group; $R^1$ is hydrogen atom; $R^2$ is hydrogen or bromine atom; $R^3$ is an aliphatic acyloxy group containing from 2 to 4 carbon atoms, benzoyloxy group, benzyloxy group, or a group of benzoyloxy or benzyloxy in which the aromatic ring is substituted with fluorine or chlorine; and $R^4$ and $R^5$ are same or different and each represents hydrogen atom, an alkyl group containing from 1 to 4 carbon atoms or an alkoxy group containing from 1 to 4 carbon atoms.

There have been known mevalonic acid derivatives which exhibit the inhibitory activity to cholesterol biosynthesis (F. M. Singer et al, Proceedings of the Society for Experimental Biology and Medicine, 102, 370 (1959); F. H. Hulcher, Archives of Biochemistry and Biophysics, 146, 422(1971)), however, the activity is not always considered to be satisfactory. The present inventors have long studied mevalonolactone derivatives and found that the novel compounds of the above general formula (I) exhibit a powerful inhibitory activity to the biosynthesis of cholesterol.

It is, accordingly, a primary object of the present invention to provide a new class of mevalonolactone derivatives which has a utility as hypolipidemic agents.

It is another object of this invention to provide processes for the preparation of such mevalonolactone derivatives.

Representative examples of mevalonolactone derivatives of general formula (I) are as follows:

(1) 3-Hydroxy-3-methyl-5-(p-benzyloxyphenyl)-5-pentanolide
(2) 3-Hydroxy-3-methyl-5-[p-(p-chlorobenzyloxy)phenyl]5-pentanolide
(3) 3-Hydroxy-3-methyl-5-[p-(p-chlorophenoxy)phenyl]5-pentanolide
(4) 3-Hydroxy-3-methyl-4-bromo-5-(p-benzyloxyphenyl)-5-pentanolide
(5) 3-Hydroxy-3-methyl-5-(4-biphenylyl)-5-pentanolide
(6) 3-Hydroxy-3-methyl-4-bromo-5-(4-biphenylyl)-5-pentanolide
(7) 3-Hydroxy-3-methyl-7-phenyl-5-heptanolide
(8) 3-Hydroxy-3-methyl-4-bromo-7-phenyl-5-heptanolide
(9) 3-Hydroxy-3,4-dimethyl-7-phenyl-5-heptanolide
(10) 3-Hydroxy-3-methyl-7-(p-hydroxyphenyl)-5-heptanolide
(11) 3-Acetoxy-3-methyl-7-(p-benzyloxyphenyl)-5-heptanolide
(12) 3-Acetoxy-3-methyl-7-(p-acetoxyphenyl)-5-heptanolide
(13) 3-Benzoyloxy-3-methyl-7-(p-benzoyloxyphenyl)-5-heptanolide
(14) 3-Hydroxy-3-methyl-7-(p-benzoyloxyphenyl)-5-heptanolide
(15) 3-Hydroxy-3-methyl-7-[p-(p-chlorobenzoyloxy)phenyl]5-heptanolide
(16) 3-Hydroxy-3-methyl-7-(p-benzyloxyphenyl)-5-heptanolide
(17) 3-Hydroxy-3-methyl-7-(m-benzyloxyphenyl)-5-heptanolide
(18) 3-Hydroxy-3-methyl-7-(o-benzyloxyphenyl)-5-heptanolide
(19) 3-Hydroxy-3-methyl-4-bromo-7-(p-benzyloxyphenyl)-5-heptanolide
(20) 3-Hydroxy-3-methyl-4-bromo-7-(n-benzyloxyphenyl)-5-heptanolide
(21) 3-Hydroxy-3-methyl-4-bromo-7-(o-benzylo phenyl)-5-heptanolide
(22) 3-Hydroxy-3-methyl-7-[p-(p-fluorobenzyloxy)phenyl]5-heptanolide
(23) 3-Hydroxy-3-methyl-7-[p-(p-chlorobenzyloxy)phenyl]5-heptanolide
(24) 3-Hydroxy-3-methyl-4-bromo-7-[p-(p-fluorobenzyloxy)phenyl]-5-heptanolide
(25) 3-Hydroxy-3-methyl-7-(p-phenethyloxyphenyl)-5-heptanolide
(26) 3-Hydroxy-3-methyl-7-(p-cinnamyloxyphenyl)-5-heptanolide
(27) 3-Hydroxy-3-methyl-7-(p-chlorophenyl)-5-heptanolide
(28) 3-Hydroxy-3-methyl-4-bromo-7-(p-chlorophenyl)-5-heptanolide
(29) 3-Hydroxy-3-methyl-7-(p-methoxyphenyl)-5-heptanolide
(30) 3-Hydroxy-3-methyl-7-(p-trifluoromethylphenyl)-5-heptanolide
(31) 3-Hydroxy-3-methyl-7-(p-phenoxyphenyl)-5-heptanolide
(32) 3-Hydroxy-3-methyl-7-(4-biphenylyl)-5-heptanolide
(33) 3-Hydroxy-3-methyl-7-(4,4'-chlorobiphenylyl)-5-heptanolide
(34) 3-Hydroxy-3-methyl-7-phenyl-6-hepten-5-olide
(35) 3-Hydroxy-3-methyl-4-bromo-7-phenyl-6-hepten-5-olide
(36) 3-Hydroxy-3,4-dimethyl-7-phenyl-6-hepten-5-olide
(37) 3-Hydroxy-3-methyl-7-(p-benzyloxyphenyl)-6-hepten-5-olide
(38) 3-Hydroxy-3-methyl-7-(o-benzyloxyphenyl)-6-hepten-5-olide
(39) 3-Hydroxy-3-methyl-7-[p-(p-chlorobenzyloxy)phenyl]6-hepten-5-olide
(40) 3-Hydroxy-3-methyl-7-(p-phenoxyphenyl)-6-hepten-5-olide
(41) 3-Hydroxy-3-methyl-8-(p-hydroxyphenyl)-5-octanolide
(42) 3-Hydroxy-3-methyl-8-(p-benzoyloxyphenyl)-5-octanolide
(43) 3-Acetoxy-3-methyl-8-(p-benzyloxyphenyl)-5-octanolide
(44) 3-Hydroxy-3-methyl-8-(p-benzyloxyphenyl)-5-octanolide
(45) 3-Hydroxy-3-methyl-8-(m-benzyloxyphenyl)-5-octanolide
(46) 3-Hydroxy-3-methyl-8-o-benzyloxyphenyl)-5-octanolide
(47) 3-Hydroxy-3-methyl-4-bromo-8-(p-benzyloxyphenyl)5-octanolide
(48) 3-Hydroxy-3-methyl-8-[p-(p-chlorobenzyloxy)phenyl]5-octanolide
(49) 3-Hydroxy-3-methyl-8-(p-phenoxyphenyl)-5-octanolide
(50) 3-Hydroxy-3-methyl-5-(p-benzyloxy-o,o'-dimethylphenyl)-5-pentanolide
(51) 3-Hydroxy-3-methyl-5-(p-benzyloxy-m-methoxyphenyl)-5-pentanolide
(52) 3-Hydroxy-3-methyl-5-(m,m',p-trimethoxyphenyl)-5-pentanolide
(53) 3-Hydroxy-3-methyl-7-(p-benzyloxy-o,o'-dimethylphenyl)-5-heptanolide
(54) 3-Hydroxy-3-methyl-7-[p-(p-chlorobenzyloxy)-o,o'-dimethylphenyl]-5-heptanolide
(55) 3-Hydroxy-3-methyl-7-(p-benzyloxy-m-methoxyphenyl)5-heptanolide
(56) 3-Hydroxy-3-methyl-7-[p-(p-chlorobenzyloxy)-m-methoxyphenyl)-5-heptanolide
(57) 3-Hydroxy-3-methyl-7-(m,m',p-trimethoxyphenyl)-5-heptanolide
(58) 3-Hydroxy-3-methyl-4-bromo-7-(p-benzyloxy-o,o'-dimethylphenyl)-5-heptanolide
(59) 3-Hydroxy-3-methyl-7-(p-benzoyloxy-o,o'-dimethylphenyl)-5-heptanolide
(60) 3-Hydroxy-3-methyl-7-(p-hydroxy-o,o'-dimethylphenyl)-5-heptanolide
(61) 3-Hydroxy-3-methyl-7-(p-hydroxy-m-methoxyphenyl)-5-heptanolide
(62) 3-Hydroxy-3-methyl-7-(p-acetoxy-m-methoxyphenyl)-5-heptanolide
(63) 3-Hydroxy-3-methyl-7-(p-benzyloxy-o,o'-dimethylphenyl)-6-hepten-5-olide
(64) 3-Hydroxy-3-methyl-7-(p-benzyloxy-m-methoxyphenyl)6-hepten-5-olide

(65) 3-Hydroxy-3-methyl-7-(m,m',p-trimethoxyphenyl)-6-hepten-5-olide
(66) 3-Hydroxy-3-methyl-8-(p-benzyloxy-o,o'-dimethylphenyl)-5-octanolide
(67) 3-Hydroxy-3-methyl-8-(p-benzyloxy-m-methoxyphenyl)5-octanolide
(68) 3-Hydroxy-3-methyl-8-(m,m',p-trimethoxyphenyl)-5-octanolide
(69) 3-Hydroxy-3-methyl-4-bromo-8-(p-benzyloxy-o,o'-dimethylphenyl)-5-octanolide
(70) 3-Hydroxy-3-methyl-8-(p-hydroxy-o,o'-dimethylphenyl)-5-octanolide
(71) 3-Hydroxy-3-methyl-8-(p-hydroxy-m-methoxyphenyl)-5-octanolide
(72) 3-Hydroxy-3-methyl-8-[p-(p-chlorobenzyloxy)-o,o'-dimethylphenyl]-5-octanolide
(73) 3-Hydroxy-3-methyl-8-[p-(p-chlorobenzyloxy)-m-methoxyphenyl]-5-octanolide The compounds of the invention may be prepared by the following processes.

Process I

A mevalonolactone derivative of formula (I) can be prepared by

[First step]

reacting a compound of formula (II):

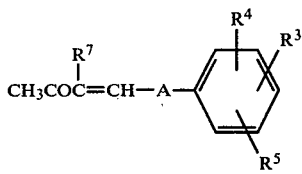

(wherein $R^7$ is hydrogen atom or methyl group, A, $R^3$, $R^4$ and $R^5$ are the same as defined above) with a compound of formula (III):

XCH$_2$COOR$^8$                        (III)

(wherein $R^8$ represents a lower alkyl group such as methyl, n-propyl or isopropyl, and X is a halogen atom such as chlorine, bromine or iodine) in the presence of a metal or metallic compound under the conditions of Reformatsky reaction to give a compound of formula (IV):

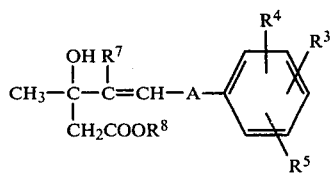

(wherein A, $R^3$, $R^4$, $R^5$, $R^7$ and $R^8$ are the same as defined above) and

[Second step]

hydrolyzing the compound of formula (IV) in a basic medium, and then reacting the resulting product with a halogenating agent to yield a compound of formula (V):

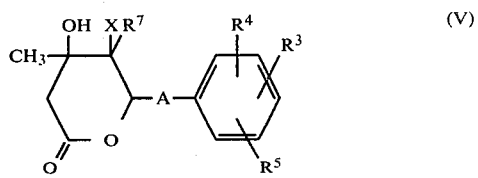

(wherein A, $R^3$, $R^4$, $R^5$, $R^7$ and X are the same as defined above), and, if necessary, subjecting the compound of formula (V)

[Third step]

to reduction and/or

[Fourth step]

acylation to produce the desired mevalonolactone derivative of formula (I).

The first step is the process for producing a hydroxycarboxylic acid ester compound (IV) which comprises reacting a keto compound (II) with a lower alkyl ester of halogenoacetic acid (III) in the presence of a metal or metallic compound under the reaction conditions usually employed for Reformatsky reaction.

As the metal or metallic compound to be employed in the reaction can be used without any particular limitation those which are usually employed for Reformatsky reaction, for example, zinc metal, zinc compounds such as di-n-propylzinc or zinc metal-diethylaluminum chloride, magnesium metal or cadmium compounds such as di-n-propylcadmium, and methyl bromoacetate or ethyl bromoacetate is preferably used as the halogenoacetic acid esters. The reaction is carried out in the presence of a solvent, and the preferable solvents to be used are aromatic hydrocarbons such as benzene or toluene, or ethers such as ethyl ether, tetrahydrofuran or dioxane. The reaction temperature and the reaction time may be varied depending upon the kind of the starting material and the metal compound to be employed or the like, but the reaction is preferably carried out usually at 0° C. to 110° C. for 2 to 7 hours.

The second step is the process for producing a halogenomevalonolactone compound (V) which comprises hydrolyzing a hydroxycarboxylic acid ester compound (IV) in a basic medium and reacting a hydroxycarboxylic acid thus formed with a halogenating agent in the presence or absence of a base.

The hydrolyzing reaction is carried out under the reaction conditions usually empolyed for basic hydrolysis, and the hydrolyzing agents preferably used are bases, for example, alkali metal hydroxide such as sodium hydroxide or potassium hydroxide, or alkali metal carbonate such as sodium carbonate or potassium carbonate. The reaction is carried out in the presence of a solvent, and the preferable solvents to be employed are water, alcohols such as methanol, ethanol or n-propanol, or the mixtures of these alcohols and water. As to the reaction temperature and the reaction time, there is no particular limitation, but the reaction is usually carried out at the temperature of from room temperature to around the reflux temperature of the solvent used for 1 to 3 hours.

Subsequently, the halo-lactonizing reaction in which a halogenomevalonolactone compounds (V) are produced by contacting a hydroxycarboxylic acid prepared as above with a halogenating agent, is carried out in the presence or absence of a base, and the halogenating agents preferably employed are halogens such as chlorine, bromine or iodine, halogenoamide compounds such as N-bromosuccinimide, N-chlorosuccinimide or N-bromoacetamide, or hypohalogenous acid compounds such as tert-butyl hypochlorite or acetyl hypobromite. The reaction is accelerated in the presence of a base, and the bases to be preferably used are such inorganic bases as alkali metal hydrogen carbonates such as sodium hydrogen carbonate or potassium hydrogen carbonate, or alkali metal carbonates such as sodium carbonate or potassium carbonate, or such organic bases as triethylamine or pyridine. The reaction is carried out in the presence of a solvent, and the solvents may be used without any particular limitation, but water, aqueous alcohols such as aqueous methanol or aqueous ethanol, aqueous aliphatic carboxylic acid dialkylamides such as aqueous dimethylformamide or aqueous dimethylacetamide, or halogenated hydrocarbons such as chloroform or carbon tetrachloride are preferably employed. The reaction temperature may be varied depending upon the kind of the halogenating agent and the base to be used or the like, but the reaction is usually carried out at the relatively low temperature of −70° C. to 0° C. The reacton time may be varied depending upon the reaction temperature or the like, but is usually from 1 to 3 hours.

The third step is the process for producing a mevalonolactone compound of formula (VI):

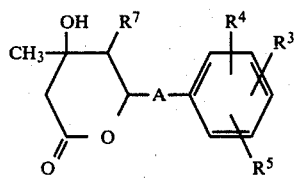

(wherein A, $R^3$, $R^4$, $R^5$ and $R^7$ are the same as defined above) which comprises reducing a halogenomevalonolactone compound (V).

The reducing agents to be employed for this purpose are not particularly limited so far as they are able to reductively remove only the halogen atom without affecting other moieties of the molecule, and tin hydride compounds such as tri-n-butyltin hydride, triphenyltin hydride or diphenyltin hydride; borohydride compounds such as sodium cyanoborohydride, tetra-n-butylammonium cyanoborohydride or sodium cyano-9-borobicyclo(3.3.1)nonanyl borohydride; sodium borohydride-dimethylsulfoxide; zinc-acetic acid; zinc-ethanol; or catalytic reduction catalyst such as palladium-charcoal and hydrogen are preferably used. When the catalytic reduction catalyst such as palladium-charcoal is used as reducing agent in this step, the compound (VI) wherein the substituent $R^3$, $R^4$ and/or $R^5$ are hydroxy group can be obtained by hydrogenolyzing the compound (V) wherein the substituent $R^3$, $R^4$ and/or $R^5$ are a hydroxy-protecting group, that is, phenylalkoxy group like benzyloxy with removing the halogen atom. The reaction is carried out in the presence of a solvent, and as the preferable solvents there are mentioned alcohols such as methanol or ethanol, ethers such as ethyl ether or tetrahydrofuran, aromatic hydrocarbons such as benzene or toluene, dialkylsulfoxides such as dimethylsulfoxide, or phosphoric acid amides such as hexamethylphosphoroamide. The reaction temperature and the reaction time may be varied depending upon the kind of the reducing agent employed or the like, but the reaction is usually carried out at room temperature to 100° C. for 3 to 48 hours.

The fourth step is the process for producing a mevalonolactone compound of formula (VII):

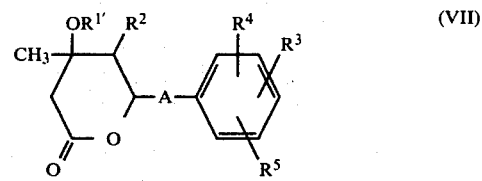

(wherein $R^{1'}$ has the same meaning except hydrogen atom as described for $R^1$ representing an acyl group, A, $R^2$, $R^3$, $R^4$ and $R^5$ are the same as defined above) which comprises reacting a compound (V) or (VI) with a reactive derivative of a carboxylic acid of formula (VIII):

$$R^{1'}OH \qquad\qquad (VIII)$$

(wherein $R^{1'}$ is the same as defined above) under the reaction conditions employed for a usual acylating reaction.

As to the acylating agents employed, there is no particular limitation so far as they are the usual reactive derivative of carboxylic acid, but as the preferable examples may be mentioned acid anhydrides such as acetic anhydride, propionic anhydride or benzoic anhydride, or acid halides such as acetyl chloride, propionyl bromide, isobutyryl chloride, α-methylbutyryl chloride, caproyl chloride, octanoyl chloride, benzoyl chloride, p-fluorobenzoyl chloride or p-chlorobenzoyl chloride. The reaction is preferably carried out in the presence of a base, and the bases to be used are organic bases such as pyridine, N,N-dimethyl-4-pyridinamine or triethylamine, but N,N-dimethyl-4-pyridineamine is most preferable.

When the compound (V) or (VI) wherein the substituent $R^3$, $R^4$ and/or $R^5$ are hydroxy group is used in this step, the compound (VII) wherein the substituent $R^3$, $R^4$ and/or $R^5$ represent an acyloxy group can be obtained with acylation of tertiary hydroxy group, but without using N,N-dimethyl-4-pyridineamine as the base, the compound wherein only phenolic hydroxy group is acylated may be mainly produced.

The reaction is carried out in the presence or absence of a solvent, and halogenated hydrocarbons such as chloroform or methylene chloride are preferably used as the solvent. As to the reaction temperature and the reaction time there is no particular limitation, but the reaction is usually carried out at 0° C. to room temperature for 1 to 12 hours.

After the reaction is completed, the desired compound prepared in each of the above steps can be recovered from the reaction mixture by a conventional way, for example, by extracting the reaction mixture with an organic solvent, drying the organic solvent layer and then evaporating the solvent. The desired compound so obtained, if necessary, may be further purified by a conventional manner, for example, recrystallization, column chromatography or the like method.

Process II

A mevalonolactone derivative of formula (I) wherein $R^1$ is hydrogen atom and $R^2$ represents hydrogen atom or methyl group, namely, a compound of formula (VI):

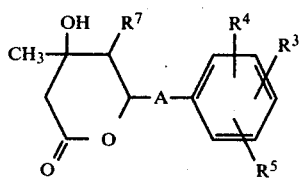

(wherein A, $R^3$, $R^4$, $R^5$ and $R^7$ are the same as defined above) can be prepared by

[First step]

reacting a compound of formula (IX):

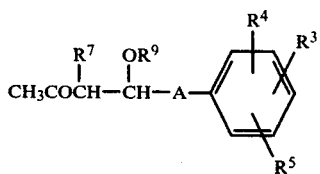

(wherein $R^9$ represents a protecting acyl group such as acetyl, propionyl, n-butyryl, isobutyryl or benzoyl, A, $R^3$, $R^4$, $R^5$ and $R^7$ are the same as defined above) with a compound of formula (III):

$$XCH_2COOR^8 \qquad (III)$$

(wherein $R^8$ and X are the same defined above) in the presence of a metal or metallic compound under the conditions of Reformatsky reaction to give a compound of formula (X):

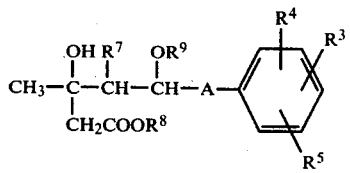

(wherein A, $R^3$, $R^4$, $R^5$, $R^7$, $R^8$ and $R^9$ are the same as defined above) and

[Second step]

hydrolyzing the compound of formula (X) in a basic medium, and then treating the resulting product under the acidic condition to produce the desired mevalonolactone derivative of formula (VI).

The first step is the process for producing a hydroxycarboxylic acid ester compound (X) which comprises reacting a keto compound (IX) with a lower alkyl ester of halogenoacetic acid of the above general formula (III) in the presence of a metal or metallic compound under the reaction conditions usually employed for Reformatsky reaction, and the conditions of the present step are the same as described above for the first step of the Process I.

The second step is the alternative process for producing a mevalonolactone compound (VI) which comprises hydrolyzing a hydroxycarboxylic acid ester compound (X) in a basic medium, neutralizing and then allowing to stand the reaction mixture under the acidic conditions.

The hydrolysis of a compound (X) is carried out under the reaction conditions usually employed for basic hydrolysis, and the hydrolyzing agents and the reaction conditions employed are the same as described for the second step of the Process I.

Subsequently, the reaction in which a mevalonolactone compound (VI) is produced from a product obtained by basic hydrolysis is carried out by allowing to stand the reaction mixture under the acidic conditions. The acids may be used without any particular limitation, but mineral acids such as hydrochloric acid or sulfuric acid, or aromatic sulfonic acids such as p-toluenesulfonic acid or benzenesulfonic acid are preferably employed. The reaction is carried out in the presence of a solvent, and the solvents preferably used are water, alcohols such as methanol or ethanol, organic acid esters such as methyl acetate or ethyl acetate, or aromatic hydrocarbons such as benzene or toluene. There is no particular limitation as to the reaction temperature and the reaction time, but the reaction is usually carried out by allowing to stand at room temperature for 6 hours to 4 days.

After the reaction is completed, the desired compound prepared in each of the above steps can be recovered from the reaction mixture by a conventional way, for example, extracting the reaction mixture with an organic solvent, drying the organic solvent layer and then evaporating the solvent. The desired compound so obtained, if necessary, may be further purified by a conventional manner, for example, recrystallization, column chromatography or the like method.

The mevalonolactone derivatives thus obtained were found to inhibit specifically the activity of 3-hydroxy-3-methylglutaryl coenzyme A reductase which is known as the rate limiting enzyme in the process of cholesterol biosynthesis. The inhibitory activity of these compounds to cholesterol biosynthesis was estimated in vitro according to the method described in H. J. Knauss et al, Journal of Biological Chemistry, 234, 2835 (1959), and the activity was expressed by the mole concentration $[I_{50}(M)]$ for 50% inhibition of the enzyme activity (Assay Method A).

The inhibitory activity of these compounds to cholesterol biosynthesis was further evaluated according to the method described in A. A. Kandutsch et al, Journal of Biological Chemistry, 248, 8408 (1973) by measuring the amount of $^{14}C$-cholesterol biosynthesized from $^{14}C$-acetic acid using L-cells of mice (929), and the activity was expressed by the mole concentration $[I_{50}(M)]$ for 50% inhibition of cholesterol biosynthesis (Assay Method B).

The inhibitory activities of the compound evaluated by the Assay Methods A and B are summarized in Table 1.

TABLE 1

Inhibitory Activities to Cholesterol Biosynthesis

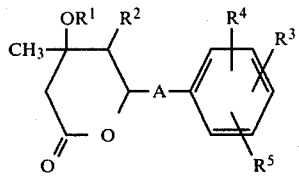

| Medicine | $R^1$ | $R^2$ | $R^3$ | $R^4$ | $R^5$ | A | $ID_{50}(M)$ Assay Method A | Assay Method B |
|---|---|---|---|---|---|---|---|---|
| Compound |  |  |  |  |  |  |  |  |
| A | H | H | p-OCH$_2$Ph | H | H | Direct linkage | $6.2 \times 10^{-5}$ | $1.3 \times 10^{-4}$ |
| B | H | H | p-Ph | H | H | Direct linkage | $1.0 \times 10^{-4}$ | $1.6 \times 10^{-4}$ |
| C | H | H | H | H | H | CH$_2$—CH$_2$ | $3.6 \times 10^{-4}$ | $4.2 \times 10^{-5}$ |
| D | H | Br | H | H | H | CH$_2$—CH$_2$ | $1.0 \times 10^{-4}$ | — |
| E | H | CH$_3$ | H | H | H | CH$_2$—CH$_2$ | $6.7 \times 10^{-5}$ | — |
| F | H | H | p-OH | H | H | CH$_2$—CH$_2$ | $6.6 \times 10^{-5}$ | — |
| G | COCH$_3$ | H | p-OCH$_2$Ph | H | H | CH$_2$—CH$_2$ | $4.5 \times 10^{-5}$ | $3.1 \times 10^{-5}$ |
| H | H | H | p-OCH$_2$Ph | H | H | CH$_2$—CH$_2$ | $4.2 \times 10^{-6}$ | $6.0 \times 10^{-6}$ |
| I | H | H | O—OCH$_2$Ph | H | H | CH$_2$—CH$_2$ | $3.3 \times 10^{-5}$ | $5.0 \times 10^{-5}$ |
| J | H | Br | p-OCH$_2$Ph | H | H | CH$_2$—CH$_2$ | $5.6 \times 10^{-6}$ | $3.0 \times 10^{-5}$ |
| K | H | Br | O—OCH$_2$Ph | H | H | CH$_2$—CH$_2$ | $4.7 \times 10^{-5}$ | $8.8 \times 10^{-5}$ |
| L | H | H | p-OCH$_2$PhF(p) | H | H | CH$_2$—CH$_2$ | — | $5.0 \times 10^{-5}$ |
| M | H | H | p-OCH$_2$Phcl(p) | H | H | CH$_2$—CH$_2$ | — | $1.9 \times 10^{-5}$ |
| N | H | H | p-cl | H | H | CH$_2$—CH$_2$ | $4.5 \times 10^{-5}$ | $3.0 \times 10^{-5}$ |
| O | H | Br | p-cl | H | H | CH$_2$—CH$_2$ | $6.3 \times 10^{-5}$ | — |
| P | H | H | p-OCH$_3$ | H | H | CH$_2$—CH$_2$ | $6.3 \times 10^{-5}$ | — |
| Q | H | CH$_3$ | H | H | H | CH=CH | $6.4 \times 10^{-5}$ | — |
| R | H | H | p-OCH$_2$Ph | H | H | CH=CH | $8.6 \times 10^{-6}$ | $1.3 \times 10^{-5}$ |
| S | H | H | m-OCH$_2$Ph | H | H | CH=CH | $7.1 \times 10^{-5}$ | $1.2 \times 10^{-4}$ |
| T | H | H | p-OCH$_2$Ph | H | m-OCH$_3$ | CH$_2$—CH$_2$ | $2.1 \times 10^{-5}$ | $1.1 \times 10^{-5}$ |
| U | H | H | p-OCH$_2$Ph | O—CH$_3$ | O'—CH$_3$ | CH$_2$—CH$_2$ | $3.8 \times 10^{-6}$ | $5.4 \times 10^{-6}$ |
| V | H | Br | p-OCH$_2$Ph | O—CH$_3$ | O'—CH$_3$ | CH$_2$—CH$_2$ | $5.2 \times 10^{-6}$ | $1.0 \times 10^{-5}$ |
| W | H | H | p-OAC | H | m-OCH$_3$ | CH$_2$—CH$_2$ | $4.5 \times 10^{-5}$ | $8.3 \times 10^{-5}$ |
| X | H | H | p-OCOPh | O—CH$_3$ | O'—CH$_3$ | CH$_2$—CH$_2$ | $3.9 \times 10^{-6}$ | $6.5 \times 10^{-6}$ |
| Y | H | H | p-OCH$_2$Ph | H | H | CH$_2$—CH$_2$—CH$_2$ | $4.0 \times 10^{-6}$ | $7.0 \times 10^{-6}$ |
| Z | H | Br | p-OCH$_2$Ph | H | H | CH$_2$—CH$_2$—CH$_2$ | $6.7 \times 10^{-6}$ | $1.2 \times 10^{-5}$ |
| Reference Medicine; Clofibrate |  |  |  |  |  |  | $1.0 \times 10^{-3}$ | $8.0 \times 10^{-5}$ |

As can be seen from the results given above, the mevalonolactone derivatives of the general formula (I) have the effect to reduce plasma lipid owing to their inhibition of cholesterol biosynthesis and are thereform useful as medicine for the treatment of the hyperlipidemia and atherosclerosis.

Accordingly, the invention also provides a pharmaceutical composition comprising at least one compound of formula (I) together with a pharmaceutical carrier or diluent. The pharmaceutical composition can be formulated in the conventional manner, using solid or liquid pharmaceutical carriers or diluents and optionally also pharmaceutical adjuvants of a type suited to the intended mode of administration. The compounds may be administered orally in the form of, for example, tablets, capsules, granules or powders, or parenterally by injectable preparations. The dose to be administered will depend upon the dosage form, and symtoms, age, body weight or the like of the patient, but the adult dosage is preferably from 200 to 2,000 mg per day, which may be given in a single dose or in divided doses, 1–4 times per day.

The methods for preparing the novel mevalonolactone derivatives (I) according to the present invention are described more in detail below by giving Examples and Preparations.

EXAMPLE 1

3-Hydroxy-3-methyl-4-bromo-7-phenyl-5-heptanolide (a) A mixture of 5.91 g of 6-phenyl-3-hexen-2-one and 4.68 g of ethyl bromoacetate was dissolved in 15 ml of a solvent mixture of benzene-ethyl ether (4:1) and the solution was dropwise added onto 2.29 g of zinc under heating and reflux. After completion of the addition the reflux was continued for 1 hour, the reaction mixture was filtered and the solvent was removed by distillation from the filtrate to give 8.0 g of a residue, which was purified through a chromatography using 200 g of silica gel affording 6.90 g of ethyl 3-hydroxy-3-methyl-7-phenyl-4-heptenoate.

(b) To a solution of 15.0 g of ethyl 3-hydroxy-3-methyl-7-phenyl-4-heptenoate in 30 ml of methanol was added 30 ml of 4 N sodium hydroxide under cooling and the mixture was stirred at room temperature for 4 hours. After completion of the hydrolysis, the reaction mixture was washed with ethyl ether, acidified with hydrochloric acid and then extracted with ethyl ether. In 200 ml of water containing 13.0 g of sodium hydrogen carbonate was dissolved 13.4 g of the carboxylic acid obtained from the above extract, and 7 ml of bromine was dropwise added to the solution under cooling at 0° C. to precipitate an oily substance. After stirring at 0° C. for 1 hour, the mixture was extracted with ethyl acetate, the extract was dried over anhydrous sodium sulfate and the solvent was removed by distillation to give a residue, which by recrystallization from a mixture of acetone and n-hexane (1:5) afforded 10.8 g of the desired compound as colorless crystals melting at 156°–158° C.

IR spectrum $\nu$ cm$^{-1}$ (nujol): 3450, 1710, 1600, 1490.

NMR spectrum $\delta$(CDCl$_3$): 1.41 (3H, singlet), 1.6–3.2 (6H, multiplet), 4.01 (1H, doublet), 4.73 (1H, multiplet), 7.27 (5H, singlet).

Elemental analysis for $C_{14}H_{17}O_3Br$: Calculated: C, 53.67; H, 5.41; Br, 25.56; Found: C, 53.76; H, 5.21; Br, 25.41.

EXAMPLE 2

3-Hydroxy-3-methyl-7-phenyl-5-heptanolide (a) To a solution of 200 mg of 3-hydroxy-3-methyl-4-bromo-7-phenyl-5-heptanolide in 2 ml of anhydrous tetrahydrofuran was added 500 mg of tri-n-butyltin hydride and the mixture was allowed to stand overnight at room temperature. After completion of the reaction, tetrahydrofuran was evaporated and n-hexane was added to the residue to precipitate an oily substance, which was purified by a thin layer chromatography (silica gel) affording 82 mg of the desired compound.

IR spectrum $\nu$ cm$^{-1}$ (liquid film): 3440, 1710, 1600, 1495.

NMR spectrum $\delta$(CDCl$_3$): 1.28 (3H, singlet), 1.5–2.2 (4H, multiplet), 3.3 (1H, broad singlet), 4.6 (1H, multiplet), 7.10 (5H, singlet).

(b) Using 1.48 g of 4-acetoxy-6-phenylhexan-2-one, 1 ml of ethyl bromoacetate and 0.62 g of zinc, the reaction and the purification of the product were carried out according to the method described in Example 1 (a) affording 1.03 g of ethyl 3-hydroxy-3-methyl-5-acetoxy-7-phenylheptanoate. The ester (0.90 g) thus obtained was dissolved in 5 ml of methanol and 2 ml of 4 N sodium hydroxide was added thereto. The mixture was stirred for 4 hours at room temperature, acidified by the addition of 4 N hydrochloric acid, 5 ml of ethyl acetate was added and the mixture was stirred for 3 days. The usual treatment of the organic solvent layer afforded 400 mg of the desired compound.

EXAMPLE 3

3-Hydroxy-3-methyl-4-bromo-7-(p-chlorophenyl)-5-heptanolide (a) Using 7.17 g of 6-(p-chlorophenyl)-3-hexen-2-one, 4.2 ml of ethyl bromoacetate and 2.47 g of zinc, the reaction and the purification of the product were carried out according to the method described in Example 1 (a) affording 6.4 g of ethyl 3-hydroxy-3-methyl-7-(p-chlorophenyl)-4-heptenoate.

(b) The carboxylic acid (2.88 g) prepared by hydrolyzing 3.27 g of ethyl 3-hydroxy-3-methyl-7-(p-chlorophenyl)-4-heptenoate with 4 N sodium hydroxide solution in methanol, was treated with 1.3 g of bromine in an aqueous sodium hydrogen carbonate solution and the reaction mixture was worked up according to the method described in Example 1 (b). The product was purified by a column chromatography using silica gel affording 1.93 g of the desired compound melting at 116°–119° C.

IR spectrum $\nu$ cm$^{-1}$ (nujol): 3600, 1720, 1500.

NMR spectrum $\delta$(CDCl$_3$): 1.41 (3H, singlet), 1.8–3.2 (7H, multiplet), 4.03 (1H, doublet), 4.70 (1H, multiplet), 7.0–7.4 (4H, multiplet).

Elemental analysis for $C_{14}H_{17}O_3BrCl$: Calculated: C, 48.35; H, 4.60; Found: C, 48.39; H, 4.61

EXAMPLE 4

3-Hydroxy-3-methyl-7-(p-chlorophenyl)-5-heptanolide

The product obtained by reducing 200 mg of 3-hydroxy-3-methyl-4-bromo-7-(p-chlorophenyl)-5-heptanolide with 680 mg of tri-n-butyltin hydride in 5 ml of anhydrous tetrahydrofuran according to the method described in Example 2 (a), was recrystallized from a mixture of n-hexane and benzene (5:1) to give 89 mg of the desired compound melting at 61°–64° C.

IR spectrum $\nu$ cm$^{-1}$ (nujol): 3450, 1695, 1490.

NMR spectrum $\delta$(CDCl$_3$): 1.37 (3H, singlet), 1.5–2.3 (4H, multiplet), 2.37 (1H, singlet), 2.5–3.0 (4H, multiplet), 4.70 (1H, multiplet), 7.0–7.4 (4H, multiplet).

Elemental analysis for $C_{14}H_{17}O_3Cl$: Calculated: C, 62.57; H, 6.33; Cl, 13.22; Found: C, 63.00; H, 6.36; Cl, 13.08.

EXAMPLE 5

3-Hydroxy-3-methyl-4-bromo-7-(p-benzyloxyphenyl)-5-heptanolide (a) Using 25.83 g of 6-(p-benzyloxyphenyl)-3-hexen-2-one, 11.3 ml of ethyl bromoacetate and 6.63 g of zinc, the reaction and the purification of the product were carried out according to the method described in Example I (a) affording 29.6 g of ethyl 3-hydroxy-3-methyl-7-(p-benzyloxyphenyl)-4-heptenoate.

(b) The carboxylic acid (22.4 g) prepared by hydrolyzing 29.6 g of ethyl 3-hydroxy-3-methyl-7-(p-benzyloxyphenyl)-4-heptenoate with 80 ml of 4 N sodium hydroxide solution in 500 ml of methanol, was treated with 9.73 g of bromine in an aqueous sodium hydrogen carbonate solution and the reaction mixture was worked up according to the method described in Example 1 (b). The product was recrystallized from a mixture of n-hexane and acetone (10:1) to yield 13.5 g of the desired compound melting at 155°–160° C.

IR spectrum $\nu$ cm$^{-1}$ (nujol): 3480, 1720, 1615, 1585, 1515.

NMR spectrum $\delta$(d$_6$-acetone): 1.43 (3H, singlet), 1.8–3.2 (6H, multiplet), 4.2–4.9 (3H, multiplet), 5.11 (2H, singlet), 7.10 (4H, quartet), 7.4–7.8 (5H, multiplet).

Elemental analysis for $C_{21}H_{23}O_4Br$: Calculated: C, 60.14; H, 5.49; Br, 19.07; Found: C, 60.01; H, 5.45; Br, 19.15.

EXAMPLE 6

3-Hydroxy-3-methyl-7-(p-benzyloxyphenyl)-5-heptanolide

The product obtained by reducing 2.0 g of 3-hydroxy-3-methyl-4-bromo-7-(p-benzyloxyphenyl)-5-heptanolide with 5.59 g of tri-n-butyltin hydride in 50 ml of anhydrous tetrahydrofuran according to the method described in Example 2 (a), was recrystallized from a mixture of n-hexane and ethyl ether (5:1) to give 1.44 g of the desired compound melting at 82°–85° C.

IR spectrum $\nu$ cm$^{-1}$ (nujol): 3440, 1700, 1615, 1585, 1520.

NMR spectrum $\delta$(d$_6$-acetone): 1.30 (3H, singlet), 1.6–2.1 (4H, multiplet), 2.4–3.0 (4H, multiplet), 4.00 (1H, singlet), 4.6 (1H, multiplet), 5.10 (2H, singlet), 7.09 (4H, quartet), 7.3–7.6 (5H, multiplet).

Elemental analysis for $C_{21}H_{24}O_4$: Calculated: C, 74.11; H, 7.06; Found: C, 74.25; H, 7.18.

EXAMPLE 7

3-Hydroxy-3,4-dimethyl-4-bromo-7-phenyl-6-hepten-5-olide (a) Using 8.60 g of 3-methyl-6-phenyl-3,5-hexadien-2-one, 8.0 ml of ethyl bromoacetate and 4.60 g of zinc, the reaction and the purification of the product were carried out according to the method described in Example 1 (a) affording 12.20 g of ethyl 3-hydroxy-3,4-dimethyl-7-phenyl-4,6-heptadienoate.

(b) The carboxylic acid (1.09 g) prepared by hydrolyzing 12.20 g of ethyl 3-hydroxy-3,4-dimethyl-7-phenyl-4,6-heptadienoate with 4 N sodium hydroxide solution in 60 ml of methanol, was dissolved in a solution of 700 mg of sodium hydrogen carbonate in 40 ml of a solvent mixture of water-methanol (1:1) and a solution of 1.06 g of bromine in 1 ml of methanol was dropwise added thereto under cooling at $-30°\sim 35°$ C. After stirring for 30 minutes, the crystals produced were collected by filtration, washed with water, dried, and recrystallized from a mixture of n-hexane and ethyl acetate (5:1) to give 750 mg of the desired compound melting at 121°-123° C.

IR spectrum $\nu$ cm$^{-1}$ (nujol): 3550, 1735, 1660.

NMR spectrum $\delta$(d$_6$-DMSO): 1.37 (3H, singlet), 1.78 (3H, singlet), 2.88 (2H, quartet), 5.67 (1H, doublet), 6.51 (1H, quartet), 6.91 (1H, doublet).

Elemental analysis for $C_{15}H_{17}O_3Br$: Calculated: C, 55.38; H, 5.23; Br, 24.61; Found: C, 55.89; H, 5.19; Br, 24.57.

EXAMPLE 8

3-Hydroxy-3,4-dimethyl-7-phenyl-6-hepten-5-olide

The product obtained by reducing 680 mg of 3-hydroxy-3,4-dimethyl-4-bromo-7-phenyl-6-hepten-5-olide with 6.0 g of tri-n-butyltin hydride in 10 ml of anhydrous tetrahydrofuran according to the method described in Example 2 (a), was purified by a thin layer chromatography affording 250 mg of the desired compound as an oily substance.

IR spectrum $\nu$ cm$^{-1}$ (liquid film): 3480, 1700.

NMR spectrum $\delta$(CDCl$_3$): 1.02 (3H, doublet), 1.32 (3H, singlet), 1.5-2.1 (1H, multiplet), 2.61 (2H, singlet), 4.90 (1H, quartet), 6.14 (1H, quartet), 6.73 (1H, doublet), 7.2-7.5 (5H, multiplet).

EXAMPLE 9

3-Hydroxy-3-methyl-7-(p-hydroxyphenyl)-5-heptanolide

To a solution of 5.65 g of 3-hydroxy-3-methyl-7-(p-benzyloxyphenyl)-5-heptanolide in 50 ml of ethyl acetate was added 2.0 g of 5% palladium-charcoal and the mixture was subjected to a catalytic hydrogenation. After filtration the solvent was evaporated to give crystals, which were recrystallized from a mixture of n-hexane and acetone (5:1) affording 2.56 g of the desired compound melting at 135°-137° C.

IR spectrum $\nu$ cm$^{-1}$ (nujol): 3300, 1700, 1615, 1595, 1620.

NMR spectrum $\delta$(d$_6$-acetone): 1.33 (3H, singlet), 1.6-2.0 (4H, multiplet), 2.5-2.9 (4H, multiplet), 4.00 (1H, broad singlet), 4.68 (1H, multiplet), 6.80 (2H, doublet), 7.12 (2H, doublet), 8.00 (1H, broad multiplet).

Elemental analysis for $C_{14}H_{18}O_4$: Calculated: C, 67.20; H, 6.60; Found: C, 67.25; H, 6.55.

EXAMPLE 10

3-Hydroxy-3-methyl-4-bromo-7-(o-benzyloxyphenyl)-5-heptanolide (a) Using 2.42 g of 6-(o-benzyloxyphenyl)-3-hexen-2-one, 1.8 ml of ethyl bromoacetate and 1.1 g of zinc, the reaction and the purification of the product were carried out according to the method described in Example 1 (a) affording 2.9 g of ethyl 3-hydroxy-3-methyl-7-(o-benzyloxyphenyl)-4-heptenoate.

(b) The carboxylic acid (2.15 g) prepared by hydrolyzing ethyl 3-hydroxy-3-methyl-7-(o-benzyloxyphenyl)-4-heptenoate was treated with 1.6 g of bromine in an aqueous methanol solution of sodium hydrogen carbonate and the reaction mixture was worked up according to the method described in Example 1 (b). The product was recrystallized from ether to give 2.3 g of the desired compound melting at 122°-125° C.

IR spectrum $\nu$ cm$^{-1}$ (nujol): 3480, 1710, 1600, 1590, 1500.

NMR spectrum $\delta$(CDCl$_3$): 1.35 (3H, singlet), 2.0-3.2 (6d, multiplet), 3.97 (1H, doublet), 4.74 (1H, multiplet), 5.11 (2H, singlet), 6.7-7.1 (9H, multiplet).

Elemental analysis for $C_{21}H_{23}O_4Br$: Calculated: C, 60.25; H, 5.50; Br, 19.12; Found: C, 60.01; H, 5.49; Br, 19.09.

EXAMPLE 11

3-Hydroxy-3-methyl-7-(o-benzyloxyphenyl)-5-heptanolide

The product obtained by reducing 0.489 g of 3-hydroxy-3-methyl-4-bromo-7-(o-benzyloxyphenyl)-5-heptanolide with 1.34 g of the tri-n-butyltin hydride in 4 ml of anhydrous tetrahydrofuran according to the method described in Example 2 (a), was purified by a thin layer chromatography affording 0.300 g of the desired compound as an oily substance.

IR spectrum $\nu$ cm$^{-1}$ (liquid film): 3500, 1710, 1600, 1500, 1485.

NMR spectrum $\delta$(CDCl$_3$): 1.28 (3H, singlet), 1.5-2.2 (4H, multiplet), 2.3-3.1 (4H, multiplet), 4.77 (1H, multiplet), 5.17 (2H, singlet), 6.8-7.7 (9H, multiplet).

EXAMPLE 12

3-Hydroxy-3-methyl-7-(p-benzyloxyphenyl)-6-hepten-5-olide (a) Using 3.07 g of 6-(p-benzyloxyphenyl)-3,5-hexadien-2-one, 2 ml of ethyl bromoacetate and 1.1 g of zinc, the reaction and the purification of the product were carried out according to the method described in Example 1 (a) affording an ethyl ester, which was hydrolyzed with 20 ml of 4 N sodium hydroxide solution in 40 ml of ethanol to give 2.66 g of 3-hydroxy-3-methyl-7-(p-benzyloxyphenyl)-4,6-heptadiene carboxylic acid.

(b) In a mixture of 20 ml of ethanol and 20 ml of water were dissolved 1.00 g of 3-hydroxy-3-methyl-7-(p-benzyloxyphenyl)-4,6-heptadiene carboxylic acid and 0.50 g of sodium hydrogen carbonate and a solution of 1.10 g of iodine in 10 ml of ethanol was added thereto under ice-cooling. After stirring for 1 hour, the reaction mixture was extracted with ethyl acetate and the solvent evaporated to give 1.20 g of yellow crystals. To a solution of 1.13 g of the yellow crystals thus obtained in 20 ml of dimethoxyethane was added 2.86 g of tri-n-butyltin hydride and the mixture was stirred for 24 hours. The crystals obtained by the usual treatment were recrystallized from a solvent mixture of acetone and ether (1:5) to yield 200 mg of the desired compound melting at 155°–156° C.

IR spectrum $\nu$ cm$^{-1}$ (nujol): 3480, 1730, 1610, 1580, 1520, 1240.

NMR spectrum $\delta$(d$_6$-acetone): 1.37 (3H, singlet), 1.8–2.2 (2H, multiplet), 2.57 (2H, singlet), 4.42 (1H, singlet), 5.17 (2H, singlet), 5.30 (1H, multiplet), 6.20 (1H, quartet), 6.75 (1H, doublet), 6.9–7.6 (9H, multiplet).

Elemental analysis for $C_{21}H_{22}O_4$: Calculated: C, 74.56; H, 6.51; Found: C, 74.52; H, 6.57.

EXAMPLE 13

3-Hydroxy-3-methyl-7-(m-benzyloxyphenyl)-6-hepten-5-olide

Using 5.80 g of 6-(m-benzyloxyphenyl)-3,5-hexadien-2-one, 7 ml of ethyl bromoacetate and 2.8 g of zinc, the reaction was carried out according to the method described in Example 12 (a) affording an ester compound, from which there was obtained 5.34 g of a carboxylic acid by the hydrolysis. The thus obtained carboxylic acid (1.56 g) and 0.77 g of sodium hydrogen carbonate were dissolved in a mixture of 20 ml of methanol and 20 ml of water and the solution was treated with 1.5 g of iodine according to the method described in Example 12 (b) affording crystals, which were reduced with 4.4 g of tri-n-butyltin hydride to give 0.501 g of the desired compound. After recrystallization from a mixture of acetone and ether (1:10) it showed a melting point of 122.5°–124° C.

IR spectrum $\nu$ cm$^{-1}$ (nujol): 3420, 1705, 1610, 1580, 1490.

NMR spectrum $\delta$(CDCl$_3$): 1.33 (3H, singlet), 1.6–2.3 (2H, multiplet), 2.4–2.7 (2H, multiplet), 3.17 (1H, broad singlet), 5.05 (2H, singlet), 5.33 (1H, multiplet), 6.18 (1H, quartet), 6.72 (1H, doublet), 6.8–7.6 (9H, multiplet).

Elemental analysis for $C_{21}H_{22}O_4$: Calculated: C, 74.55; H, 6.50; Found: C, 74.32; H, 6.42.

EXAMPLE 14

3-Hydroxy-3-methyl-4-bromo-5-(p-benzyloxyphenyl)-5-pentanolide

Using 8.30 g of 4-(p-benzyloxyphenyl)-3-buten-2-one, 5.5 ml of ethyl bromoacetate and 3.21 g of zinc, the reaction and the purification of the product were carried out according to the method described in Example 1 (a) to yield an ethyl ester compound, from which there was obtained 9.0 g of a carboxylic acid by the hydrolysis. The thus obtained carboxylic acid and 6.56 g of sodium hydrogen carbonate were dissolved in 200 ml of a mixture of methanol-water (1:1) and the solution was treated with 1.93 ml of bromine affording 7.7 g of the desired compound as crystals melting at 157°–162° C.

IR spectrum $\nu$ cm$^{-1}$ (nujol): 3450, 1720, 1620, 1595, 1520.

NMR spectrum $\delta$(d$_6$-acetone): 1.50, 1.53 (3H, doublet), 2.98 (2H, doublet), 4.57, 4.69 (1H, quartet), 5.16 (2H, singlet), 5.43, 5.65 (1H, quartet), 7.0–7.7 (9H, multiplet).

Elemental analysis for $C_{19}H_{19}O_3Br$: Calculated: C, 60.80; H, 5.07; Found: C, 61.05; H, 5.06.

EXAMPLE 15

3-Hydroxy-3-methyl-5-(p-benzyloxyphenyl)-5-pentanolide

The product obtained by reducing 2.0 g of 3-hydroxy-3-methyl-4-bromo-5-(p-benzyloxyphenyl)-5-pentanolide with 5.99 g of tri-n-butyltin hydride in 40 ml of anhydrous tetrahydrofuran according to the method described in Example 2 (a), was separated by a thin layer chromatography into two isomers in a total yield of 1.40 g.

Isomer 1 m.p. 128°–129° C.

IR spectrum $\nu$ cm$^{-1}$ (nujol): 3480, 1730, 1620, 1590, 1520.

NMR spectrum $\delta$(CDCl$_3$): 1.38 (3H, singlet), 1.8–3.1 (4H, multiplet), 3.37 (1H, broad singlet), 5.17 (2H, singlet), 5.72 (1H, quartet), 7.17 (4H, quartet), 7.42 (5H, singlet).

Elemental analysis for $C_{19}H_{20}O_4$: Calculated: C, 73.08; H, 6.41; Found: C, 73.20; H, 6.50.

Isomer 2 m.p. 146°–148° C.

IR spectrum $\nu$ cm$^{-1}$ (nujol): 3410, 1710, 1610, 1580, 1515.

NMR spectrum $\delta$(CDCl$_3$): 1.48 (3H, singlet), 2.19 (1H, doublet), 2.21 (1H, doublet), 2.55 (2H, singlet), 3.54 (1H, broad singlet), 5.09 (2H, singlet), 5.24 (1H, quartet), 7.18 (4H, quartet), 7.42 (5H, singlet).

Elemental analysis for $C_{19}H_{20}O_4$: Calculated: C, 73.08; H, 6.41; Found: C, 73.05; H, 6.45.

EXAMPLE 16

3-Hydroxy-3-methyl-4-bromo-7-(p-[p-fluorobenzyloxy)phenyl]-5-heptanolide (a) Using 900 mg of 6-[p-(p-fluorobenzyloxy)phenyl]-3-hexen-2-one, 660 mg of ethyl bromoacetate and 260 mg of zinc, the reaction and the purification of the product were carried out according to the method described in Example 1 (a) affording 1.10 g of ethyl 3-hydroxy-3-methyl-7-[p-(p-fluorobenzyloxy)phenyl]-4-heptenoate.

(b) The carboxylic acid (900 mg) prepared by hydrolyzing 1.03 g of ethyl 3-hydroxy-3-methyl-7-[p-(p-fluorobenzyloxy)phenyl]-4-heptenoate with 4 N sodium hydroxide solution in methanol, was treated with 0.2 ml of bromine in an aqueous sodium hydrogen carbonate solution and the reaction mixture was worked up according to the method described in Example 1 (b). The product was recrystallized from a mixture of acetone and ethyl ether (1:10) to yield 1.2 g of the desired compound melting at 160°–163° C.

IR spectrum $\nu$ cm$^{-1}$ (nujol): 3460, 1715, 1610, 1600, 1580, 1515, 1500.

NMR spectrum $\delta$(d$_6$-acetone): 1.39 (3H, singlet), 2.2–3.0 (4H, multiplet), 2.82 (2H, singlet), 4.36 (1H, doublet), 4.73 (1H, sextet), 5.10 (2H, singlet), 6.9–7.6 (8H, multiplet).

Elemental analysis for $C_{21}H_{22}Br\ FO_4$; Calculated: C, 57.67; H, 5.03; Found: C, 57.00; H, 4.50.

EXAMPLE 17

3-Hydroxy-3-methyl-7-[p-(p-fluorobenzyloxy)phenyl]-5-heptanolide

The product obtained by reducing 200 mg of 3-hydroxy-3-methyl-4-bromo-7-[p-(p-fluorobenzyloxy)phenyl]-5-heptanolide with 400 mg of tri-n-butyltin hydride in 2 ml of anhydrous tetrahydrofuran according to the method described in Example 2 (a), was recrystallized from a mixture of acetone and n-hexane (1:5) to give 99 mg of the desired compound melting at 143.5°–144.5° C.

IR spectrum $\nu$ cm$^{-1}$ (nujol): 3450, 1700, 1613, 1605, 1585, 1518.

NMR spectrum $\delta$(CDCl$_3$): 1.33 (3H, singlet), 1.5–3.0 (8H, multiplet), 4.67 (1H, multiplet), 5.03 (2H, singlet), 6.8–7.6 (8H, multiplet).

Elemental analysis for $C_{21}H_{23}FO_4$: Calculated: C, 70.39; H, 6.42; Found: C, 71.02; H, 6.70

EXAMPLE 18

3-Hydroxy-3-methyl-4-bromo-5-(4-biphenylyl)-5-pentanolide

Using 3.60 g of 4-(4-biphenylyl)-3-buten-2-one, 2.7 ml of ethyl bromoacetate and 1.58 g of zinc, the reaction and the purification of the product were carried out according to the method described in Example 1 (a) affording an ethyl ester compound, from which there was obtained 1.8 g of a carboxylic acid by the hydrolysis. The thus obtained carboxylic acid (1.60 g) and 1.29 g of sodium hydrogen carbonate were dissolved in 60 ml of a solvent mixture of methanol and water (2:1) and the solution was treated with 0.38 ml of bromine. The product thus prepared was recrystallized from a mixture of n-hexane and acetone (10:1) to give 1.3 g of the desired compound melting at 173°–176° C.

IR spectrum $\nu$ cm$^{-1}$ (nujol): 3460, 1700, 1600, 1480.

NMR spectrum $\delta$(d$_6$-acetone): 1.52 (3H, singlet), 3.02 (1H, singlet), 3.08 (2H, doublet), 3.13 (1H, doublet), 5.74 (1H, doublet), 7.3–7.9 (9H, multiplet).

Elemental analysis for $C_{18}H_{17}O_3Br$: Calculated: C, 59.83; H, 4.71; Br, 22.13; Found: C, 59.91; H, 4.54; Br, 22.44.

EXAMPLE 19

3-Hydroxy-3-methyl-5-(4-biphenylyl)-5-pentanolide

The product obtained by reducing 0.50 g of 3-hydroxy-3-methyl-4-bromo-5-(4-biphenylyl)-5-pentanolide with 1.62 g of tri-n-butyltin hydride in 10 ml of anhydrous tetrahydrofuran according to the method described in Example 2 (a), was recrystallized from a mixture of n-hexane and acetone (10:1) to give 0.20 g of the desired compound melting at 151°–153° C.

IR spectrum $\nu$ cm$^{-1}$ (nujol): 3450, 1700, 1600, 1570, 1485.

NMR spectrum $\delta$(d$_6$-acetone): 1.41 (3H, singlet), 2.0–2.4 (2H, multiplet), 4.22 (1H, singlet), 4.33 (2H, singlet), 5.79 (1H, quartet), 7.3–7.9 (9H, multiplet).

Elemental analysis for $C_{18}H_{18}O_3$: Calculated: C, 76.60; H, 6.38; Found: C, 76.72; H, 6.40.

According to the same methods as described in Examples 1 and 2 (a), the following compounds (Examples 20–22) can be prepared.

EXAMPLE 20

3-Hydroxy-3-methyl-7-[p-(p-chlorobenzyloxy)phenyl]-5-heptanolide m.p. 160°–163° C.

IR spectrum $\nu$ cm$^{-1}$ (nujol): 3500, 1710, 1610, 1600, 1585, 1510.

NMR spectrum $\delta$(d$_6$-DMSO): 1.38 (3H, singlet), 1.5–2.1 (4H, multiplet), 2.4–2.9 (4H, multiplet), 4.25 (1H, multiplet), 4.93 (1H, singlet), 5.08 (2H, singlet), 6.93 (2H, doublet), 7.03 (2H, doublet), 7.47 (4H, singlet).

Elemental analysis for $C_{21}H_{23}ClO_4$: Calculated: C, 67.29; H, 6.14; Found: C, 67.65; H, 5.92.

EXAMPLE 21

3-Hydroxy-3,4-dimethyl-7-phenyl-5-heptanolide m.p. 106°–109° C.

IR spectrum $\nu$ cm$^{-1}$ (nujol): 3500, 1705, 1605, 1500.

NMR spectrum $\delta$ (CDCl$_3$): 0.98 (3H, doublet), 1.28 (3H, singlet), 1.5–2.4 (3H, multiplet), 2.4–3.1 (5H, multiplet), 4.38 (1H, multiplet), 7.28 5H, singlet).

Elemental analysis for $C_{15}H_{20}O_3$: Calculated: C, 72.58; H, 8.06; Found: C, 72.30; H, 8.10.

EXAMPLE 22

3-Hydroxy-3-methyl-7-(p-methoxyphenyl)-5-heptanolide m.p. 76°–78° C.

IR spectrum $\nu$ cm$^{-1}$ (nujol): 3410, 1690, 1615, 1590, 1520.

NMR spectrum $\delta$ (CDCl$_3$): 1.32 (3H, singlet), 1.5–2.2 (4H, multiplet), 2.4–3.0 (5H, multiplet), 3.78 (3H, singlet), 4.71 (1H, multiplet), 6.84 (2H, doublet), 7.15 (2H, doublet).

Elemental analysis for $C_{15}H_{20}O_4$: Calculated: C, 68.18; H, 7.58; Found: C, 68.23; H, 7.59.

EXAMPLE 23

3-Acetoxy-3-methyl-7-(p-benzyloxyphenyl)5-heptanolide

One hundred milligrams of 3-hydroxy-3-methyl-7-(p-benzyloxyphenyl)-5-heptanolide was dissolved in 0.1 ml of methylene chloride and 0.63 ml of acetic anhydride, 0.50 ml of triethylamine and 1.5 mg of N,N-dimethyl-4-pyridineamine were added thereto under cooling at 0° C. After allowing to stand under ice-cooling for 4 hours, the reaction mixture was poured into ice-water and the crystals thus precipitated were recrystallized from a mixture of ethyl acetate and n-hexane (1:10) affording 68 mg of the desired compound melting at 98°–101° C.

IR spectrum $\nu$ cm$^{-1}$ (nujol): 1730, 1720, 1610, 1580, 1510, 1240, 1220.

NMR spectrum $\delta$ (CDCl$_3$): 1.60 (3H, singlet), 1.99 (3H, singlet), 1.2–2.2 (4H, multiplet), 2.3–3.6 (5H, multiplet), 4.50 (1H, multiplet), 5.12 (2H, singlet), 7.14 (4H, multiplet), 7.3–7.6 (5H, multiplet).

Elemental analysis for $C_{23}H_{26}O_5$: Calculated: C, 72.25; H, 6.81; Found: C, 72.21; H, 6.88.

EXAMPLE 24

3-Acetoxy-3-methyl-7-(p-acetoxyphenyl)5-heptanolide

By acetylating 110 mg of 3-hydroxy-3-methyl-7-(p-hydroxyphenyl)-5-heptanolide according to the method described in Example 23, there was obtained 90 mg of the desired compound melting at 72°–75° C.

IR spectrum $\nu$ cm$^{-1}$ (nujol): 1740, 1720, 1500, 1220.

NMR spectrum $\delta$ (CDCl$_3$): 1.60 (3H, singlet), 2.00 (3H, singlet), 2.30 (3H, singlet), 1.7–2.3 (4H, multiplet), 2.6–3.2 (4H, multiplet), 4.47 (1H, multiplet), 7.18 (4H, multiplet).

Elemental analysis for $C_{18}H_{22}O_6$: Calculated: C, 64.67; H, 6.59; Found: C, 64.81; H, 6.52.

EXAMPLE 25

3-Hydroxy-3-methyl-4-bromo-7-(p-benzyloxy-o,o'-dimethylphenyl)-5-heptanolide (a) A mixture of 5.77 g of 6-(p-benzyloxy-o,o'-dimethylphenyl)-3-hexen-2-one and 2.5 ml of ethyl bromoacetate was dissolved in 30 ml of benzene and the solution was dropwise added onto 1.46 g of zinc under heating and refluxing. After completion of the addition, the reflux was continued for 1 hour. The reaction mixture was filtered and the solvent was removed by distillation from the filtrate to give 7.0 g of a residue, which was purified by a chromatography using 250 g of silica gel affording 5.20 g of ethyl 3-hydroxy-3-methyl-7-(p-benzyloxy-o,o'-dimethylphenyl)-4-heptaenoate.

(b) To a solution of 5.10 g of ethyl 3-hydroxy-3-methyl-7-(p-benzyloxy-o,o'-dimethylphenyl)-4-heptenoate in 45 ml of methanol was added 7 ml of 4 N sodium hydroxide under cooling and the mixture was stirred for 4 hours at room temperature. After completion of the hydrolysis the reaction mixture was washed with ethyl ether, acidified with hydrochloric acid and then extracted with ethyl ether. To a solution of 4.77 g of the carboxylic acid obtained from the extract in 40 ml of methanol was added 1.4 g of sodium hydrogen carbonate and then 0.68 ml of bromine was dropwise added thereto under chilling at $-70°$ C. to $-65°$ C. and the stirring was continued for 1 hour at the same temperature. A saturated sodium hydrogen carbonate solution was then added to the reaction mixture below 0° C., and the mixture was extracted with ethyl acetate. The extract was dried over anhydrous sodium sulfate, the solvent was evaporated and the residue was recrystallized from a mixture of acetone and n-hexane (1:10) affording 5.11 g of the desired compound as colorless crystals melting at 146°–147° C.

IR spectrum $\nu$ cm$^{-1}$ (nujol): 3375, 1705, 1605, 1585, 1500.

NMR spectrum $\delta$ (d$_6$-DMSO): 1.30 (3H, singlet), 1.8–3.0 (6H, multiplet), 2.27 (6H, singlet), 4.43 (1H, doublet), 4.4–4.8 (1H, multiplet), 5.07 (2H, singlet), 6.72 (2H, singlet), 7.60 (5H, singlet).

Elemental analysis for C$_{23}$H$_{27}$BrO$_4$: Calculated: C, 61.74; H, 6.04; Br, 17.90; Found: C, 61.33; H, 5.81; Br, 18.30.

EXAMPLE 26

3-Hydroxy-3-methyl-7-(p-benzyloxy-o,o'-dimethylphenyl)-5-heptanolide

To a solution of 1.34 g of 3-hydroxy-3-methyl-4-bromo-7-(p-benzyloxy-o,o'-dimethylphenyl)-5-heptanolide in 13 ml of anhydrous tetrahydrofuran was added 2.52 g of tri-n-butyltin hydride and the mixture was heated under reflux for 2 hours. After completion of the reaction, tetrahydrofuran was evaporated and n-hexane was added to the residue to precipitate an oily substance, which was crystallized from a mixture of ethyl acetate and isopropyl ether (1:10) to yield 870 mg of the desired compound melting at 157°–159° C.

IR spectrum $\nu$ cm$^{-1}$ (nujol): 3370, 1700, 1610, 1585.

NMR spectrum $\delta$ (CDCl$_3$): 1.36 (3H, singlet), 1.5–2,0 (4H, multiplet), 2.30 (6H, singlet), 2.4–3.0 (4H, multiplet), 4.5–5.0 (1H, multiplet), 5.03 (2H, singlet), 6.70 (2H, singlet), 7.42 (5H, singlet)

Elemental analysis for C$_{23}$H$_{28}$O$_4$: Calculated: C, 75.00; H, 7.61; Found: C, 74.69; H, 7.71.

EXAMPLE 27

3-Hydroxy-3-methyl-7-(p-hydroxy-o,o'-dimethylphenyl)-5-heptanolide

A solution of 500 mg of 3-hydroxy-3-methyl-7-(p-benzyloxy-o,o'-dimethylphenyl)-5-heptanolide in 20 ml of ethyl acetate was subjected to a catalytic hydrogenation using 500 mg of 5% palladium-charcoal. After the reaction was completed palladium-charcoal was removed by filtration, ethyl acetate was evaported from the filtrate and the residue was crystallized from a mixture of acetone and n-hexane (1:5) to afford 219 mg of the desired compound melting at 181°–183° C.

IR spectrum $\nu$ cm$^{-1}$ (nujol): 3470, 3380, 1675, 1595.

NMR spectrum $\delta$ (d$_6$-DMSO): 1.22 (3H, singlet), 1.5–1.9 (4H, multiplet), 2.20 (6H, singlet), 2.3–2.9 (4H, multiplet), 4.65 (1H, multiplet), 4.90 (1H, singlet), 6.47 (2H, multiplet), 8.80 (1H, singlet), Elemental analysis for C$_{16}$H$_{22}$O$_4$: Calculated: C, 69.06; H, 7.93; Found: C, 69.15; H, 7.91.

EXAMPLE 28

3-Hydroxy-3-methyl-7-(p-benzoyloxy-o,o'-dimethylphenyl)-5-heptanolide

To a suspension of 100 mg of 3-hydroxy-3-methyl-7-(p-hydroxy-o,o'-dimethylphenyl)-5-heptanolide in 2 ml of methylene chloride were added 0.1 ml of pyridine and 0.1 ml of benzoyl chloride and the mixture was stirred for 2 hours at room temperature. After the reaction was completed, water was added to the reaction mixture, the mixture was extracted with ethyl acetate and the solvent was evaporated from the extract to give a residue, which was recrystallized from a mixture of ethyl acetate and isopropyl ether (1:10) affording 112 mg of the desired compound melting at 181°–183° C.

IR spectrum $\nu$ cm$^{-1}$ (nujol): 3430, 1730, 1700, 1595.

NMR spectrum $\delta$ (d$_6$-DMSO): 1.25 (3H, singlet), 1.5–2.0 (4H, multiplet), 2.35 (6H, singlet), 2.3–3.0 (4H, multiplet), 4.71 (1H, multiplet), 4.98 (1H, singlet), 6.98 (2H, singlet), 7.6–7.9 (3H, multiplet), 8.1–8.5 (2H, multiplet)

Elemental analysis for C$_{23}$H$_{26}$O$_5$: Calculated: C, 72.25; H, 6.81; Found: C, 72.20; H, 6.68.

According to the same methods as described in Example 28, the following compounds (Examples 29 and 30) can be prepared.

EXAMPLE 29

3-Hydroxy-3-methyl-7-(p-benzoyloxyphenyl)-5-heptanolide m.p. 118.5°–119.5° C.

IR spectrum $\nu$ cm$^{-1}$ (nujol): 3460, 1730, 1690, 1600, 1510.

NMR spectrum $\delta$ (CDCl$_3$): 1.32 (3H, singlet), 1.5–2.3 (4H, multiplet), 2.5–3.0 (4H, multiplet), 4.72 (1H, multiplet), 7.0–7.4 (4H, multiplet), 7.4–7.7 (3H, multiplet), 8.1–8.3 (2H, multiplet).

Elemental analysis for C$_{21}$H$_{22}$O$_5$: Calculated: C, 71.19; H, 6.22; Found: C, 71.12; H, 6.23.

EXAMPLE 30

3-Hydroxy-3-methyl-7-[p-(p-chlorobenzoyloxy)-phenyl]-5-heptanolide m.p. 168°–170° C.

IR spectrum $\nu$ cm$^{-1}$ (nujol): 3350, 1730, 1700, 1600, 1520.

NMR spectrum δ (CDCl$_3$): 1.35 (3H, singlet), 1.6–3.1 (8H, multiplet), 4.73 (1H, multiplet), 7.1–8.3 (8H, multiplet).

Elemental analysis for C$_{21}$H$_{21}$ClO$_5$: Calculated: C, 64.87; H, 5.41; Cl, 9.13; Found: C, 64.51; H, 5.59; Cl, 9.01

EXAMPLE 31

3-Hydroxy-3-methyl-7-(p-benzyloxy-m-methoxyphenyl)-5-heptanolide (a) Using 1.19 g of 6-(p-benzyloxy-m-methoxyphenyl)-3-hexen-2-one, 0.64 ml of ethyl bromoacetate and 0.33 g of zinc, the reaction and the purification of the product were carried out according to the method described in Example 25 (a) affording 1.28 g of ethyl 3-hydroxy-3-methyl-7-(p-benzyloxy-m-methoxyphenyl)-4-heptenoate.

(b) To a solution of 1.24 g of ethyl 3-hydroxy-3-methyl-7-(p-benzyloxy-m-methoxyphenyl)-4-heptenoate in 10 ml of ethanol was added 1.5 ml of 4 N sodium hydroxide and the mixture was allowed to stand overnight at room temperature to give a carboxylic acid. According to the method described in Example 25 (b), 1.14 g of the carboxylic acid so obtained was treated with 0.34 g of sodium hydrogen carbonate and 0.2 ml of bromine in 11 ml of methanol to afford an oily substance, which was then treated with 2.68 g of tri-n-butyltin hydride in 20 ml of anhydrous tetrahydrofuran according to the method described in Example 26. The reaction mixture was extracted with ethyl acetate, the solvent was evaporated from the extract and the residue was purified by a column chromatography using 30 g of silica gel affording 0.54 g of the desired compound.

IR spectrum $\nu$ cm$^{-1}$ (liquid film): 3450, 1710, 1603, 1590, 1515.

NMR spectrum δ (CDCl$_3$): 1.33 (3H, singlet), 1.5–2.2 (4H, multiplet), 2.3–2.9 (4H, multiplet), 3.88 (3H, singlet), 4.73 (1H, multiplet), 5.15 (3H, singlet), 6.7–7.0 (2H, multiplet), 7.3–7.5 (6H, multiplet).

Elemental analysis for C$_{22}$H$_{26}$O$_5$: Calculated: C, 71.35; H, 7.03; Found: C, 71.70; H, 7.23.

EXAMPLE 32

3-Hydroxy-3-methyl-7-(p-hydroxy-m-methoxyphenyl)-5-heptanolide

Using 140 mg of 3-hydroxy-3-methyl-7-(p-benzyloxy-m-methoxyphenyl)-5-heptanolide, 140 mg of 5% palladium-charcoal and 14 ml of ethyl acetate, the reaction and the purification of the product were carried out according to the method described in Example 27 affording 75 mg of the desired compound melting at 162°–164° C.

IR spectrum $\nu$ cm$^{-1}$ (nujol): 3420, 3330, 1680, 1600, 1520.

NMR spectrum δ (d$_6$-DMSO): 1.20 (3H, singlet), 1.5–2.1 (4H, multiplet), 2.3–2.8 (4H, multiplet), 3.78 (3H, singlet), 4.58 (1H, multiplet), 6.7–7.0 (3H, singlet), 8.58 (1H, singlet).

Elemental analysis for C$_{15}$H$_{20}$O$_5$: Calculated: C, 64.29; H, 7.14; Found: C, 64.50; H, 7.33.

EXAMPLE 33

3-Hydroxy-3-methyl-7-(p-acetoxy-m-methoxyphenyl)-5-heptanolide

To a solution of 100 mg of 3-hydroxy-3-methyl-7-(p-hydroxy-m-methoxyphenyl)-5-heptanolide in 1 ml of pyridine was added 1 ml of acetic anhydride and the mixture was stirred overnight at room temperature. After completion of the reaction, water was added to the reaction mixture and the mixture was extracted with ethyl acetate. Evaporation of the solvent from the extract yielded the desired compound as a colorless oily substance, IR spectrum $\nu$ cm$^{-1}$ (liquid film): 3450, 1765, 1715, 1605, 1510.

NMR spectrum δ (CDCl$_3$): 1.35 (3H, singlet), 1.5–2.2 (4H, multiplet), 2.30 (3H, singlet), 2.5–3.0 (4H, multiplet), 3.85 (3H, singlet), 4.76 (1H, multiplet), 6.8–7.2 (3H, multiplet).

Elemental analysis for C$_{17}$H$_{22}$O$_6$: Calculated: C, 63.35; H, 6.83; Found: C, 63.09; H. 6.74.

EXAMPLE 34

3-Hydroxy-3-methyl-4-bromo-8-(p-benzyloxyphenyl)-5-octanolide (a) Using 0.68 g of 7-(p-benzyloxyphenyl)-3-hepten-2-one, 0.37 ml of ethyl bromoacetate and 0.19 g of zinc, the reaction and the purification of the product were carried out according to the method described in Example 25 (a) affording 0.84 g of ethyl 3-hydroxy-3-methyl-8-(p-benzyloxyphenyl)-4-octenoate.

(b) According to the method described in Example 25 (b), the reaction was carried out by using 0.13 ml of bromine and 0.74 g of the carboxylic acid which was prepared from 0.80 g of ethyl 3-hydroxy-3-methyl-8-(p-benzyloxyphenyl)-4-octenoate, 8 ml of ethanol and 1 ml of 4 N sodium hydroxide, and the product was recrystallized from ethyl ether to give 0.32 g of the desired compound melting at 100°–101° C.

IR spectrum $\nu$ cm$^{-1}$ (nujol): 3480, 1720, 1615, 1590, 1520.

NMR spectrum δ (d$_6$-DMSO): 1.28 (3H, singlet), 1.5–2.1 (4H, multiplet), 2.74 (2H, doublet), 3.25 (2H, singlet), 4.33 (1H, doublet), 4.58 (1H, multiplet), 5.10 (2H, singlet), 5.50 (1H, singlet), 7.08 (4H, quartet), 7.45 (5H, multiplet).

Elemental analysis for C$_{22}$H$_{25}$Br O$_4$: Calculated: C, 60.97; H, 5.77; Found: C, 60.66; H, 5.68.

EXAMPLE 35

3-Hydroxy-3-methyl-8-(p-benzyloxyphenyl)5-octanolide

According to the method described in Example 26, the reaction and the purification of the product were carried out by using 0.26 g of 3-hydroxy-3-methyl-4-bromo-8-(p-benzyloxyphenyl)-5-octanolide, 0.51 g of tri-n-butyltin hydride and anhydrous tetrahydrofuran affording 0.18 g of the desired compound melting at 80°–81° C.

IR spectrum $\nu$ cm$^{-1}$ (liquid film): 3450, 1710, 1610, 1580, 1510.

NMR spectrum δ (CDCl$_3$): 1.32 (3H, singlet), 1.4–2.2 (6H, multiplet), 2.2–2.8 (4H, multiplet), 4.75 (1H, multiplet), 5.07 (2H, singlet), 7.03 (4H, quartet), 7.12 (5H, singlet).

Elemental analysis for C$_{22}$H$_{26}$O$_4$: Calculated: C, 74.58; H, 7.34; Found: C, 74.64; H, 7.58.

The novel compounds among the starting materials which were employed in the above Examples may be prepared by the methods as shown below in Preparations.

PREPARATION 1

6-(p-Benzyloxyphenyl)-3-hexen-2-one

A solution of 21.2 g of 3-(p-benzyloxyphenyl)propionaldehyde and 30.9 g of acetylmethylenetriphenylphosphorane in 120 ml of tetrahydrofuran was heated under reflux for 4.5 hours, the solvent was then evaporated and the residual crystals were recrystallized from a mixture of n-hexane and ether (5:1) to give 26.1 g of the desired compound melting at 70°–72° C.

IR spectrum $\nu$ cm$^{-1}$ (nujol): 1665, 1620, 1610, 1590, 1510.

NMR spectrum $\delta$ (CDCl$_3$): 2.22 (3H, singlet), 2.4–2.9 (4H, singlet), 5.08 (2H, singlet), 6.10 (1H, doublet), 6.7–7.9 (10H, multiplet).

According to the same method the following compounds can be prepared.

6-(p-Chlorophenyl)-3-hexen-2-one

IR spectrum $\nu$ cm$^{-1}$ (liquid film): 1660, 1620, 1610, 1585.

NMR spectrum $\delta$ (CDCl$_3$): 2.18 (3H, singlet), 2.4–3.0 (4H, multiplet), 6.10 (1H, doublet), 6.85 (1H, multiplet), 7.1–7.3 (4H, multiplet).

6-(o-Benzyloxyphenyl)-3-hexen-2-one

IR spectrum $\nu$ cm$^{-1}$ (liquid film): 1665, 1620, 1605, 1590.

NMR spectrum $\delta$ (CDCl$_3$): 2.24 (3H, singlet), 2.4–3.0 (4H, multiplet), 5.10 (2H, singlet), 6.12 (1H, doublet), 6.7–7.1 (9H, multiplet).

PREPARATION 2

4-(p-Benzyloxyphenyl)-3-buten-2-one

A solution of 10.0 g of p-benzyloxybenzaldehyde and 15.7 g of acetylmethylenetriphenylphosphorane in 100 ml of toluene was heated under reflux for 2 hours, the solvent was then evaporated and the residual crystals were recrystallized from ether to give 9.5 g of the desired compound melting at 106°–107° C.

IR spectrum $\nu$ cm$^{-1}$ (nujol): 1660, 1620, 1605, 1575, 1510.

NMR spectrum $\delta$ (CDCl$_3$): 2.32 (3H, singlet), 5.10 (2H, singlet), 6.61 (1H, doublet), 6.9–7.7 (10H, multiplet),

PREPARATION 3

6-(p-Benzyloxyphenyl)-3,5-hexadien-2-one

A solution of 19.7 g of p-benzyloxycinnamaldehyde and 27.6 g of acetylmethylenetriphenylphosphorane in 190 ml of xylene was heated under reflux for 2 hours, the solvent was then evaporated and the residual crystals were recrystallized from benzene to give 18.3 g of the desired compound melting at 132°–133° C.

IR spectrum $\nu$ cm$^{-1}$ (nujol): 1655, 1620, 1610, 1595, 1510, 1250.

NMR spectrum $\delta$ (CDCl$_3$): 2.27 (3H, singlet), 5.17 (2H, singlet), 6.23 (1H, doublet), 6.7–7.6 (12H, multiplet).

According to the same method the following compound can be prepared.

6-(m-Benzyloxyphenyl)-3,5-hexadien-2-one m.p. 63°–64° C.

IR spectrum $\nu$ cm$^{-1}$ (nujol): 1670, 1630, 1595, 1580, 1495, 1490.

NMR spectrum $\delta$ (CDCl$_3$): 2.28 (3H, singlet), 5.10 (2H, singlet), 6.27 (1H, doublet), 6.8–7.6 (10H, multiplet).

PREPARATION 4

6-(p-Benzyloxy-o,o'-dimethylphenyl)-3-hexen-2-one

A solution of 2.68 g of 3-(p-benzyloxy-o,o'-dimethylphenyl)propionaldehyde and 4.50 g of acetylmethylenetriphenylphosphorane in 27 ml of toluene was heated under reflux for 2 hours, toluene was then evaporated and the residue was purified by a chromatography using 30 g of silica gel affording 2.8 g of the desired compound.

IR spectrum $\nu$ cm$^{-1}$ (liquid film): 1675, 1630, 1610, 1565.

NMR spectrum $\delta$ (CDCl$_3$): 2.22 (3H, singlet), 2.28 (6H, singlet), 2.2–3.9 (4H, multiplet), 5.03 (2H, singlet), 6.13 (1H, broad doublet), 6.72 (2H, singlet), 6.92 (1H, sextet), 7.42 (1H, singlet).

Elemental analysis for $C_{21}H_{24}O_2$: Calculated: C, 81.82; H, 7.79; Found: C, 81.55; H, 7.60.

PREPARATION 5

6-(p-Benzyloxy-m-methoxyphenyl)-3-hexen-2-one

A solution of 2.3 g of 3-(p-benzyloxy-m-methoxyphenyl)propionaldehyde and 2.97 g of acetylmethylenetriphenylphosphorane in 22 ml of toluene was heated under reflux for 2 hours, toluene was then evaporated and the residue was purified by a chromatography using 30 g of silica gel and recrystallization from a mixture of ethyl ether and n-hexane (1:5) afforded 1.49 g of the desired compound melting at 59.5°–60.5° C.

IR spectrum $\nu$ cm$^{-1}$ (nujol): 1685, 1640, 1635, 1590, 1515.

NMR spectrum $\delta$ (CDCl$_3$): 2.18 (3H, singlet), 2.4–2.9 (4H, multiplet), 3.87 (3H, singlet), 5.15 (2H, singlet), 6.12 (1H, doublet), 6.6–7.1 (4H, multiplet), 7.3–7.6 (5H, multiplet).

Elemental analysis for $C_{20}H_{22}O_3$: Calculated: C, 77.42; H, 7.10; Found: C, 77.45; H, 7.22.

According to the same method the following compound can be prepared.

6-[p-(p-Fluorobenzyloxy)phenyl]-3-hexen-2-one m.p. 70.5°–71.5° C.

IR spectrum $\nu$ cm$^{-1}$ (nujol): 1680, 1640, 1605, 1590, 1520.

NMR spectrum $\delta$ (CDCl$_3$): 2.18 (3H, singlet), 2.3–3.0 (4H, multiplet), 5.02 (2H, singlet), 6.08 (1H, broad doublet), 6.6–7.6 (9H, multiplet).

Elemental analysis for $C_{19}H_{19}FO_2$: Calculated: C, 76.51; H, 6.38; F, 6.38; Found: C, 76.41; H, 6.44; F, 6.40.

PREPARATION 6

7-(p-Benzyloxyphenyl)-3-hepten-2-one

A solution of 0.7 g of 4-(p-benzyloxyphenyl)butylaldehyde and 0.96 g of acetylmethylenetriphenylphosphorane in 10 ml of toluene was heated under reflux for 2 hours, toluene was then evaporated and the residue was purified through a chromatography using 10 g of silica gel affording 0.68 g of the desired compound.

IR spectrum $\nu$ cm$^{-1}$ (liquid film): 1680, 1630, 1610, 1515.

NMR spectrum δ (CDCl₃) :2.20 (3H, singlet), 1.5–2.8 (6H, multiplet), 5.07 (2H, singlet), 6.10 (1H, sextet), 6.6–7.6 (10H, multiplet).

Elemental analysis for $C_{20}H_{22}O_2$: Calculated: C, 81.63; H, 7.48; Found: C, 81.90; H, 7.66.

PREPARATION 7

4-Acetoxy-6-phenylhexan-2-one

To a solution of 850 mg of 4-hydroxy-6-phenylhexan-2-one (T. Mukaiyama et al., Chemistry Letters 1976, 95) in 10 ml of methylene chloride were added 1 ml of acetic anhydride and 0.8 ml of pyridine under ice-cooling at 0° C., and then stirring was continued for further 1 hr at room temperature. The reaction mixture was poured into water, the methylene chloride layer was washed with water, dried over anhydrous sodium sulfate, and the solvent was evaporated to afford 1.10 g of the desired compound.

IR spectrum ν cm⁻¹ (liquid film): 3460, 1735, 1720, 1615, 1500.

NMR spectrum δ (CDCl₃): 1.35 (3H, singlet), 1.7–2.2 (4H, multiplet), 2.01 (3H, singlet), 2.5–3.0 (4H, multiplet), 4.55 (1H, multiplet), 7.32 (5H, singlet).

Elemental analysis for $C_{14}H_{18}O_3$: Calculated: C, 72.41; H, 7.76; Found: C, 72.55; H, 7.80.

What is claimed is:

1. A compound having the formula

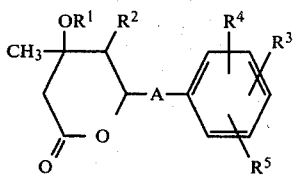

wherein A represents a vinylene group; R¹ represents a hydrogen atom, an aliphatic acyl group containing from 2 to 8 carbon atoms, benzoyl group, or a benzoyl group substituted with hydroxy, alkoxy containing from 1 to 4 carbon atoms, aliphatic acyloxy containing from 2 to 8 carbon atoms or halogen; R² represents a hydrogen atom, a halogen atom or methyl group; and R³, R⁴ and R⁵ are same or different and each represents a hydrogen atom, a halogen atom, an alkyl group containing from 1 to 4 carbon atoms with or without halogen as the substituent, phenyl group, or a phenyl group substituted with halogen, alkoxy containing from 1 to 4 carbon atoms, aliphatic acyloxy containing from 2 to 8 carbon atoms or alkyl containing from 1 to 4 carbon atoms, or a substituted alkyl containing from 1 to 4 carbon atoms with halogen as the substituent, or a group represented by the formula R⁶O—wherein R⁶ represents a (i) hydrogen atom, (ii) an aliphatic acyl group containing from 2 to 8 carbon atoms, (iii) benzoyl group, phenyl group, a phenylalkyl group comprising an alkylene chain having from 1 to 3 carbon atoms, cinnamyl group, or (iv) a group of benzoyl, phenyl, phenylalkyl comprising an alkylene chain having from 1 to 3 carbon atoms or cinnamyl in all of which the aromatic ring is substituted with hydroxy, halogen, alkoxy containing from 1 to 4 carbon atoms, aliphatic acyloxy containing from 2 to 8 atoms, an alkyl group containing from 1 to 4 carbon atoms or a substituted alkyl group containing from 1 to 4 carbon atoms with halogen as the substituent and (v) an alkyl group containing from 1 to 4 carbon atoms or a substituted alkyl group containing from 1 to 4 carbon atoms with halogen as the substituent.

2. A compound of claim 1 wherein A represents a vinylene group; R¹ is hydrogen atom, an aliphatic acyl group containing from 2 to 4 carbon atoms, benzoyl group, or a benzoyl group substituted with fluorine, chlorine or bromine; R² represents hydrogen atom, bromine atom or methyl group; R³ is hydrogen atom, fluorine atom, chlorine atom, bromine atom, trifluoromethyl group, 2,2,2-trifluoroethyl group, an alkyl group containing from 1 to 4 carbon atoms, hydroxy group, an aliphatic acyloxy group containing from 2 to 4 carbon atoms, phenyl group, benzoyloxy group, phenoxy group, benzyloxy group, phenethyloxy group, cinnamyloxy group, or a group of phenyl, benzoyloxy, phenoxy, benzyloxy, phenethyloxy or cinnamyloxy in all of which the aromatic ring is substituted with fluorine, chlorine, bromine, trifluoromethyl or 2,2,2-trifluoroethyl, or an alkoxy group containing from 1 to 4 carbon atoms; and R⁴ and R⁵ are same or different and each represents hydrogen atom, an alkyl group containing from 1 to 4 carbon atoms, hydroxy group, an aliphatic acyloxy group containing from 2 to 4 carbon atoms, benzyloxy group, phenoxy groups, benzyloxy group, phenethyloxy group, cinnamyloxy group, or a group of benzoyloxy, phenoxy, benzyloxy, phenethyloxy or cinnamyloxy in all of which the aromatic ring is substituted with fluorine, chlorine, bromine, trifluoromethyl or 2,2,2-trifluoroethyl, or an alkoxy group containing from 1 to 4 carbon atoms.

3. A compound of claim 1 wherein A represents a vinylene group; R¹ is hydrogen atom; R² is hydrogen or bromine atom; R³ is an aliphatic acyloxy group containing from 2 to 4 carbon atoms, a benzoyloxy group, a benzyloxy group, a benzoyloxy in which the aromatic ring is substituted with fluorine or chlorine, or a benzyloxy in which the aromatic ring is substituted with fluorine or chlorine; and R⁴ and R⁵ are the same or different and each represents a hydrogen atom, an alkyl group containing from 1 to 4 carbon atoms or an alkoxy group containing from 1 to 4 carbon atoms.

4. The compound of claim 1 which is 3-hydroxy-3-methyl-7-(p-benzyloxyphenyl)-6-hepten-5-olide.

5. The compound of claim 1 which is 3-hydroxy-3-methyl-7-(o-benzyloxyphenyl)-6-hepten-5-olide.

6. The compound of claim 1 which is 3-hydroxy-3-methyl-7-(p-(p-chlorobenzyloxy)phenyl)-6-hepten-5-olide.

7. The compound of claim 1 which is 3-hydroxy-3-methyl-7-(p-benzyloxy-o,o'-dimethylphenyl)-6-hepten-5-olide.

8. The compound of claim 1 which is 3-hydroxy-3-methyl-7-(p-benzyloxy-m-methoxyphenyl)-6-hepten-5-olide.

9. A process for the preparation of a compound having the formula

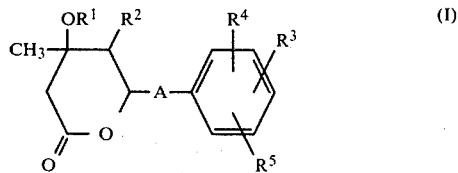

wherein A represents a vinylene group; R¹ represents a hydrogen atom, an aliphatic acyl group containing from 2 to 8 carbon atoms, benzoyl group, or a benzoyl group substituted with hydroxy, alkoxy containing from 1 to 4 carbon atoms, aliphatic acyloxy containing from 2 to 8 carbon atoms or halogen; $R^2$ represents a hydrogen atom, a halogen atom or methyl group; and $R^3$, $R^4$ and $R^5$ are same or different and each represents a hydrogen atom, a halogen atom, an alkyl group containing from 1 to 4 carbon atoms with or without halogen as the substituent, phenyl group, or a phenyl group substituted with halogen, alkoxy containing from 1 to 4 carbon atoms, aliphatic acyloxy containing from 2 to 8 carbon atoms or alkyl containing from 1 to 4 carbon atoms, or a substituted alkyl containing from 1 to 4 carbon atoms with halogen as the substituent, or a group represented by the formula $R^6O$—wherein $R^6$ represents a (i) hydrogen atom, (ii) an aliphatic acyl group containing from 2 to 8 carbon atoms, (iii) benzoyl group, phenyl group, a phenylalkyl group comprising an alkylene chain having from 1 to 3 carbon atoms, cinnamyl group, or (iv) a group of benzoyl, phenyl, phenylalkyl compising an alkylene chain having from 1 to 3 carbon atoms or cinnamyl in all of which the aromatic ring is substituted with hydroxy, halogen, alkoxy containing from 1 to 4 carbon atoms, aliphatic acyloxy containing from 2 to 8 carbon atoms, an alkyl group containing from 1 to 4 carbon atoms or a substituted alkyl group containing from 1 to 4 carbon atoms with halogen as the substituent and (v) an alkyl group containing from 1 to 4 carbon atoms or a substituted alkyl group containing from 1 to 4 carbon atoms with halogen as the substituent which comprises reacting a compound of formula

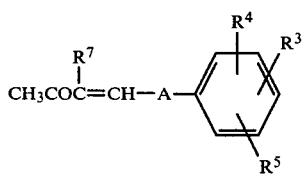

(II)

wherein $R^7$ is hydrogen atom or methyl group, A, $R^3$, $R^4$ and $R^5$ are the same as defined above with a compound of formula $$XCH_2COOR^8 \quad\quad (III)$$

wherein $R^8$ represents a lower alkyl group and X is a halogen atom in the presence of a metal or metallic compound under the conditions of Reformatsky reaction to give a compound of formula

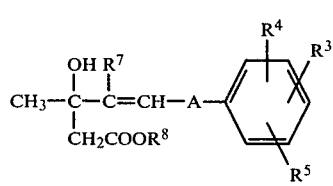

(IV)

wherein A, $R^3$, $R^4$, $R^5$, $R^7$ and $R^8$ are the same as defined above and hydrolyzing the compound of formula (IV) in a basic medium, and then reacting the resulting product with a halogenating agent to yield a compound of formula

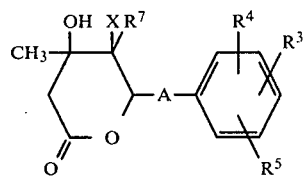

(V)

wherein A, $R^3$, $R^4$, $R^5$, $R^7$ and X are the same as defined above and, if necessary, subjecting the compound of formula (V) to reduction and/or acylation to produce said compound of formula (I).

10. A process for the preparation of a compound having the formula

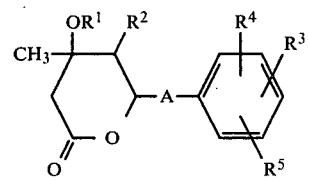

(I)

wherein A represents a vinylene group; $R^1$ represents a hydrogen atom, an aliphatic acyl group containing from 2 to 8 carbon atoms, benzoyl group, or a benzoyl group substituted with hydroxy, alkoxy containing from 1 to 4 carbon atoms, aliphatic acyloxy containing from 2 to 8 carbon atoms or halogen; $R^2$ represents a hydrogen atom, a halogen atom or methyl group; and $R^3$, $R^4$ and $R^5$ are same or different and each represents a hydrogen atom, a halogen atom, an alkyl group containing from 1 to 4 carbon atoms with or without halogen as the substituent, phenyl group, or a phenyl group substituted with halogen, alkoxy containing from 1 to 4 carbon atoms, aliphatic acyloxy containing from 2 to 8 carbon atoms or alkyl containing from 1 to 4 carbon atoms, or a substituted alkyl containing from 1 to 4 carbon atoms with halogen as the substituent, or a group represented by the formula $R^6O$—wherein $R^6$ represents a (i) hydrogen atom, (ii) an aliphatic acyl group containing from 2 to 8 carbon atoms, (iii) benzoyl group, phenyl group, a phenylalkyl group comprising an alkylene chain having from 1 to 3 carbon atoms, cinnamyl group, or (iv) a group of benzoyl, phenyl, phenylalkyl comprising an alkylene chain having from 1 to 3 carbon atoms or cinnamyl in all of which the aromatic ring is substituted with hydroxy, halogen, alkoxy containing from 1 to 4 carbon atoms, aliphatic acyloxy containing from 2 to 8 carbon atoms, an alkyl group containing from to 4 carbon atoms or a substituted alkyl group containing from 1 to 4 carbon atoms with halogen as the substituent and (v) an alkyl group containing from 1 to 4 carbon atoms or a substituted alkyl group containing from 1 to 4 carbon atoms with halogen as the substituent which comprises when $R^1$ is hydrogen atom and $R^2$ represents a hydrogen atom or methyl group, reacting a compound of formula

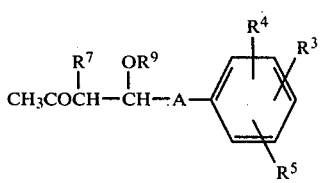

(IX)

wherein R⁹ represents a protecting acyl group, A, R³, R⁴, R⁵ and R⁷ are the same as defined above with a compound of formula

XCH₂COOR⁸ (III)

wherein R⁸ and X are the same defined above in the presence of a metal or metallic compound under the conditions of Reformatsky reaction to give a compound of formula

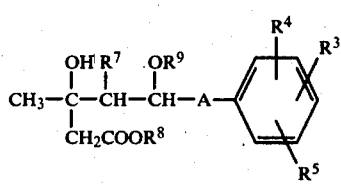 (X)

wherein A, R³, R⁴, R⁵, R⁷, R⁸ and R⁹ are the same as defined above and hydrolyzing the compound of formula (X) in a basic medium, and then treating the resulting product under the acidic conditions to produce said compound of formula (I) wherein R¹ is hydrogen atom and R² represents a hydrogen atom or methyl group.

11. A pharmaceutical composition for treating hyperlipidemia in mammals comprising an inert pharmaceutically acceptable carrier or diluent and hypolipidemic effective amount of a compound having the formula

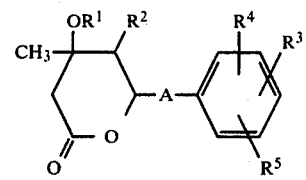 (I)

wherein A represents a vinylene group; R¹ represents a hydrogen atom, an aliphatic acyl group containing from 2 to 8 carbon atoms, benzoyl group, or a benzoyl group substituted with hydroxy, alkoxy containing from 1 to 4 carbon atoms, aliphatic acyloxy containing from 2 to 8 carbon atoms or halogen; R² represents a hydrogen atom, a halogen atom or methyl group; and R³, R⁴ and R⁵ are same or different and each represents a hydrogen atom, a halogen atom, an alkyl group containing from 1 to 4 carbon atoms with or without halogen as the substituent, phenyl group, or a phenyl group substituted with halogen, alkoxy containing from 1 to 4 carbon atoms, aliphatic acyloxy containing from 2 to 8 carbon atoms or alkyl containing from 1 to 4 carbon atoms, or a substituted alkyl containing from 1 to 4 carbon atoms with halogen as the substituent, or a group represented by the formula R⁶O— wherein R⁶ represents a (i) hydrogen atom, (ii) an aliphatic acyl group containing from 2 to 8 carbon atoms, (iii) benzoyl group, phenyl group, a phenylalkyl group comprising an alkylene chain having from 1 to 3 carbon atoms, cinnamyl group, or (iv) a group of benzoyl, phenyl, phenylalkyl comprising an alkylene chain having from 1 to 3 carbon atoms or cinnamyl in all of which the aromatic ring is substituted with hydroxy, halogen, alkoxy containing from 1 to 4 carbon atoms, aliphatic acyloxy containing from 2 to 8 carbon atoms, an alkyl group containing from 1 to 4 carbon atoms or a substituted alkyl group containing from 1 to 4 carbon atoms with halogen as the substituent and (v) an alkyl group containing from 1 to 4 carbon atoms or a substituted alkyl group containing from 1 to 4 carbon atoms with halogen as the substituent.

* * * * *